US012702375B2

(12) United States Patent
Kim

(10) Patent No.: US 12,702,375 B2
(45) Date of Patent: Aug. 11, 2026

(54) X-RAY DETECTOR COMPRISING AEC SENSOR, AND OPERATING METHOD THEREFOR

(71) Applicant: Samsung Electronics Co., Ltd., Suwon-si (KR)

(72) Inventor: Sanguk Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 224 days.

(21) Appl. No.: 18/759,422

(22) Filed: Jun. 28, 2024

(65) Prior Publication Data

US 2024/0350108 A1 Oct. 24, 2024

Related U.S. Application Data

(63) Continuation of application No. PCT/KR2022/020959, filed on Dec. 21, 2022.

(30) Foreign Application Priority Data

Dec. 28, 2021 (KR) ........................ 10-2021-0190341
Feb. 3, 2022 (KR) ........................ 10-2022-0014444

(51) Int. Cl.
*A61B 6/00* (2024.01)
*A61B 6/42* (2024.01)
*G01T 1/02* (2006.01)

(52) U.S. Cl.
CPC ............ *A61B 6/542* (2013.01); *A61B 6/4241* (2013.01); *G01T 1/02* (2013.01)

(58) Field of Classification Search
CPC .......... A61B 6/542; A61B 6/4241; G01T 1/02
See application file for complete search history.

(56) References Cited

U.S. PATENT DOCUMENTS 8,376,613 B2 2/2013 Moyers
8,873,712 B2 10/2014 Wang et al.
(Continued)

FOREIGN PATENT DOCUMENTS

CN 108888284 A 11/2018
CN 212089567 U 12/2020
(Continued)

OTHER PUBLICATIONS

European Notice of Allowance issued Dec. 16, 2025 in corresponding European Patent Application No. 22916595.6.
International Search Report and Written Opinion of the ISA for PCT/KR2022/020959 mailed Mar. 22, 2023, 8 pages.
(Continued)

*Primary Examiner* — Chih-Cheng Kao
(74) *Attorney, Agent, or Firm* — Nixon & Vanderhye, P.C.

(57) ABSTRACT

Provided are an X-ray detector automatically correcting an automatic exposure control (AEC) sensing area, based on an image obtained using an AEC sensor array, and a method of operating the X-ray detector. The X-ray detector may detect, using an AEC sensor array, X-rays that have passed through an object, obtain a one-dimensional (1D) image by quantifying a dose of the detected X-rays into a signal value, identify a symmetric point from the 1D image, based on a signal value for each pixel of the 1D image, and adjust respective locations of a plurality of AEC sensing areas so that the plurality of AEC sensing areas are symmetrical to each other with respect to the identified symmetric point.

15 Claims, 17 Drawing Sheets

(56) References Cited

U.S. PATENT DOCUMENTS

| | | | | |
|---|---|---|---|---|
| 9,417,333 | B2 | 8/2016 | Sato et al. | |
| 9,521,987 | B2 | 12/2016 | Tajima | |
| 9,649,074 | B2 | 5/2017 | Simon | |
| 9,833,214 | B2 | 12/2017 | Imamura | |
| 10,448,913 | B2 | 10/2019 | Nakaya | |
| 10,898,159 | B2 | 1/2021 | Edic et al. | |
| 11,442,029 | B2 | 9/2022 | Shin et al. | |
| 11,839,013 | B2 | 12/2023 | Niwa | |
| 2004/0149920 | A1 | 8/2004 | Ishii | |
| 2005/0169425 | A1* | 8/2005 | Takasawa | A61B 6/547 378/97 |
| 2011/0249799 | A1* | 10/2011 | Lalena | A61B 6/08 378/205 |
| 2014/0369459 | A1 | 12/2014 | Foos et al. | |
| 2015/0055753 | A1 | 2/2015 | Tajima | |
| 2019/0090839 | A1* | 3/2019 | Okuno | A61B 6/10 |
| 2022/0386983 | A1* | 12/2022 | Harder | G06T 7/11 |

FOREIGN PATENT DOCUMENTS

| | | | |
|---|---|---|---|
| EP | 2623032 | | 8/2013 |
| JP | 2013027476 | A | 2/2013 |
| JP | 2014071033 | A | 4/2014 |
| JP | 2014122903 | A | 7/2014 |
| JP | 2017074158 | A | 4/2017 |
| JP | 2018082994 | A | 5/2018 |
| JP | 2020112530 | A | 7/2020 |
| JP | 2020182667 | A | 11/2020 |
| JP | 2023018768 | A | 2/2023 |
| KR | 101198065 | B1 | 11/2012 |
| KR | 101676426 | B1 | 11/2016 |
| KR | 101848408 | B1 | 4/2018 |

OTHER PUBLICATIONS

1 Extended European Search Report dated Jan. 27, 2025 issued in European Patent Application No. 22916595.6.

* cited by examiner

X-RAY DETECTOR COMPRISING AEC SENSOR, AND OPERATING METHOD THEREFOR

CROSS-REFERENCE TO RELATED APPLICATIONS

This application is a continuation of International Application No. PCT/KR2022/020959 designating the United States, filed on Dec. 21, 2022, in the Korean Intellectual Property Receiving Office and claiming priority to Korean Patent Application Nos. 10-2021-0190341, filed on Dec. 28, 2021, and 10-2022-0014444, filed on Feb. 3, 2022, in the Korean Intellectual Property Office, the disclosures of each of which are incorporated by reference herein in their entireties.

BACKGROUND

Field

The disclosure relates to an X-ray detector including an automatic exposure control (AEC) sensor, and a method of operating the X-ray detector. For example, the disclosure relates to an X-ray detector that corrects an AEC sensing area based on an image representing a dose of X-rays detected using an AEC sensor array, and a method of operating the X-ray detector.

Description of Related Art

X-ray detectors obtain an image in an X-ray imaging apparatus. X-ray detectors detect X-rays emitted by an X-ray source (or an X-ray tube) and transmitted through an object (e.g., a patient), convert the detected X-rays into an electrical signal, and output the electrical signal to thereby generate an X-ray image. As imaging automation progresses, room X-ray imaging apparatuses (Room DR) help a radiologist's work by additionally including various automation functions, such as automatic source-detector alignment or automatic exposure control (AEC), and reduce quality deviations in captured images. AEC sensors are installed in the bucky of a room X-ray apparatus (Room DR) to detect the dose of X-rays emitted by an X-ray source in real time, convert an accumulated dose value into a voltage value, and output the voltage value. When the output voltage value exceeds a preset threshold, x-ray detectors may transmit an X-ray blocking signal to the X-ray source to block X-ray emission from the X-ray source. Accordingly, despite various photographing protocols, differences between patients, or differences between body parts to be photographed, the dose of X-rays reaching the X-ray detector may be constantly maintained, and an image quality may be maintained uniformly.

General AEC sensors are manufactured in the form of an ion chamber using air, and are placed on a front side of an X-ray detector. General AEC sensors operate in a method of applying an appropriate voltage to an ion chamber, collecting air ions ionized by X-rays, converting the amount of charge due to the air ion collection into a voltage, and amplifying and accumulating such voltages. Ion chamber AEC sensors operate by comparing a voltage value increasing in real time with a voltage value corresponding to a target dose and, when the two voltage values are consistent with each other, stopping X-ray emission by an X-ray source.

In order for an AEC sensor to operate an AEC function without any problems, a selected body part to be photographed by the AEC sensor must be accurately positioned. In the case of a room X-ray imaging apparatus (Room DR), an AEC sensor panel is located within the bucky, is thus accurately aligned with an X-ray detector, and is also aligned with an X-ray source using, for example, an electronic control system or a mechanical matching method. In addition, because a patient's anatomical area must also be matched to an AEC sensor, cross-shaped light radiation is used. In particular, in the case of a stand bucky, an AEC sensor area is marked on the surface of the stand bucky, so a radiologist positions a patient by referring to the AEC sensor area. That is, in order to use an AEC function, it is very important to align an X-ray source, a patient, an AEC sensor, and an X-ray detector with each other.

Recently, mobile X-ray detectors or portable X-ray detectors have become popular and are widely used. Mobile X-ray detectors including an AEC sensor are located at the back of a patient during X-ray imaging, so a radiologist should check the outline of the X-ray detector and the patient's anatomy by eye. Therefore, in the case of mobile X-ray detectors, the alignment between the X-ray source-patient-AEC sensor-X-ray detector may not be accurately performed.

SUMMARY

Embodiments of the disclosure provide an X-ray detector that includes an automatic exposure control (AEC) sensor and corrects an AEC sensing area.

An X-ray detector according to an example embodiment of the disclosure may include: a plurality of photodetection elements including a plurality of pixels and configured to detect X-rays, an automatic exposure control (AEC) sensor array including at least one sensor configured to detect X-rays that have passed through an object and to quantify a dose of the detected X-rays as a signal value and output the signal value, a memory storing one or more instructions, and at least one processor, comprising processing circuitry, individually and/or collectively, configured to: obtain a 1D image, based on the signal value output through the AEC sensor array; identify a symmetric point from the 1D image, based on a signal value for each pixel of the 1D image; and adjust respective locations of a plurality of AEC sensing areas so that the plurality of AEC sensing areas are symmetrical to each other with respect to the identified symmetric point.

Embodiments of the disclosure provide a method, performed by an X-ray detector including an automatic exposure control (AEC sensor), of correcting an AEC sensing area.

According to an example embodiment, the method may include: detecting X-rays that have passed through an object, using an AEC sensor array, and obtaining a one-dimensional (1D) image by quantifying a dose of the detected X-rays into a signal value; identifying a symmetric point from the 1D image, based on a signal value for each pixel of the 1D image; and adjusting respective locations of a plurality of AEC sensing areas so that the plurality of AEC sensing areas are symmetrical to each other with respect to the identified symmetric point.

Embodiments of the disclosure provide a computer program product including a computer-readable recording medium having recorded thereon a computer program.

According to an example embodiment, a non-transitory computer-readable recording medium may have recorded thereon instructions readable by an X-ray detector including an AEC sensor and which, when executed by at least one processor, individually and/or collectively, of the X-ray detector, cause the X-ray detector to perform operations including: detecting X-rays that have passed through an object, using an automatic exposure control (AEC) sensor array, and obtaining a 1D image by quantifying a dose of the detected X-rays into a signal value; identifying a symmetric point from the 1D image, based on a signal value for each pixel of the 1D image; and adjusting respective locations of a plurality of AEC sensing areas so that the plurality of AEC sensing areas are symmetrical to each other with respect to the identified symmetric point.

BRIEF DESCRIPTION OF THE DRAWINGS

This disclosure may be readily understood by reference to the following detailed description and the accompanying drawings, in which reference numerals refer to structural elements. The above and other aspects, features and advantages of certain embodiments of the present disclosure will be more apparent from the following detailed description, taken on conjunction with the accompanying drawings, in which.

DETAILED DESCRIPTION

Figure 1:
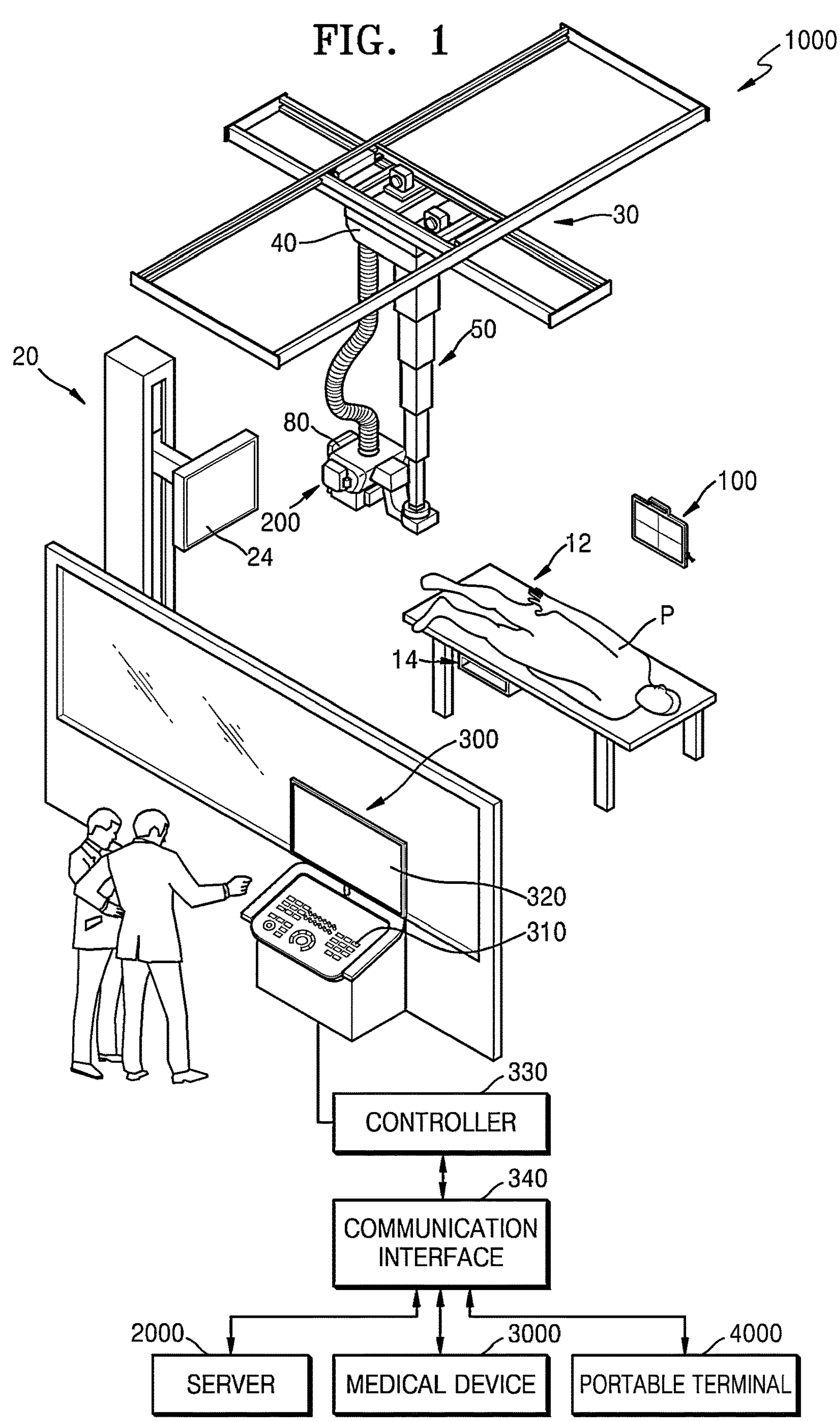
FIG. 1 is perspective view including a block diagram illustrating an example configuration of an X-ray imaging apparatus according to various embodiments.

Although general terms widely used at present were selected for describing the disclosure in consideration of the functions thereof, these general terms may vary according to intentions of one of ordinary skill in the art, case precedents, the advent of new technologies, or the like. Terms arbitrarily selected may also be used in a specific case. In this case, their meanings are given in the detailed description. Hence, the terms must be defined based on their meanings and the contents of the entire disclosure, not by simply stating the terms.

An expression used in the singular may encompass the expression of the plural, unless it has a clearly different meaning in the context. Unless otherwise defined, all terms (including technical and scientific terms) used herein have the same meaning as commonly understood by one of ordinary skill in the art to which this disclosure belongs.

The terms “comprises” and/or “comprising” or “includes” and/or “including” used herein specify the presence of stated elements, but do not preclude the presence or addition of one or more other elements. The terms “unit”, “-er (-or)”, and “module” when used in this disclosure may refer, for example, to a unit in which at least one function or operation is performed, and may be implemented as hardware, software, or a combination of hardware and software.

The expression “configured to (or set to)” used therein may be used interchangeably with, for example, “suitable for”, “having the capacity to”, “designed to”, “adapted to”, “made to”, or “capable of”, according to situations. The expression “configured to (or set to)” may not only necessarily refer to “specifically designed to” in terms of hardware. Instead, in some situations, the expression “system configured to” may refer to a situation in which the system is “capable of” together with another device or component parts. For example, the phrase “a processor configured (or set) to perform A, B, and C” may refer to a dedicated processor (such as an embedded processor) for performing a corresponding operation, or a generic-purpose processor (such as a central processing unit (CPU) or an application processor (AP)) that can perform a corresponding operation by executing one or more software programs stored in a memory.

When an element (e.g., a first element) is “coupled to” or “connected to” another element (e.g., a second element), the first element may be directly coupled to or connected to the second element, or, unless otherwise described, a third element may exist therebetween.

Throughout the disclosure, a term ‘object’ is a thing to be imaged, and may include a human, an animal, or a part of a human or animal. For example, the object may include a part of a body (e.g., an organ), a phantom, or the like.

In the disclosure, X-rays are electromagnetic waves having a wavelength of 0.01 to 100 Å and can pass through an object. Thus, they may be commonly used in a wide range of applications, such as medical equipment that take images of the inside of a living body and non-destructive testing equipment for industrial use.

In the disclosure, an 'X-ray detector' may detect X-rays emitted by an X-ray source (or an X-ray tube) and transmitted through an object, converts the detected X-rays into an electric signal, and measure the electrical signal. An X-ray detector according to an embodiment of the disclosure may include a flat panel detector (FPD) that detects an X-ray signal by accumulating signal charge in each of a plurality of pixels using a thin-film transistor (TFT) active matrix substrate in which a plurality of pixels are arranged to accumulate signal charges according to the amount of incident X-ray, and obtains X-ray image data of the object using the detected X-ray signal. However, an X-ray detector according to the disclosure is not limited thereto.

In the disclosure, an 'automatic exposure control (AEC) sensor' is configured to detect an X-ray that has passed through an object, quantify the dose of the detected X-ray as a signal value, and output the signal value. The AEC sensor according to an embodiment of the disclosure may be configured as an integrated sensor included within an X-ray detector.

In the disclosure, an 'AEC sensing area' may refer, for example, to an area set to perform an AEC function. The AEC sensing area may be set to perform an AEC function of detecting the dose of X-rays passing through an object on an imaging surface of an X-ray detector, and blocking X-rays when the detected dose of X-rays exceeds a preset threshold.

Embodiments of the disclosure are described in greater detail herein with reference to the accompanying drawings. The disclosure may, however, be embodied in many different forms and should not be construed as being limited to the examples set forth herein.

Various example embodiments of the disclosure now will be described in greater detail with reference to the accompanying drawings.

FIG. 1 is a perspective view including a block diagram illustrating an example configuration X-ray imaging apparatus 1000 according to various embodiments. FIG. 1 illustrates a room X-ray imaging apparatus (Room DR).

Referring to FIG. 1, the X-ray imaging apparatus 1000 may include an X-ray detector 100 detecting an X-ray that has passed through an object P, an X-ray radiator 200 generating an X-ray and radiating the X-ray to the object P, and a workstation 300 receiving a command from a user and providing information. The X-ray imaging apparatus 1000 may also include a controller (e.g., including processing circuitry) 330 controlling the X-ray imaging apparatus 1000 according to the received command, and a communication interface (e.g., including communication circuitry) 340 communicating with an external apparatus.

Some or all of the components of the controller 330 and the communication interface 340 may be included in the workstation 300 or may be provided separately from the workstation 300.

The X-ray radiator 200 may include an X-ray source generating an X-ray, and a collimator adjusting an irradiation region irradiated by the X-ray generated by the X-ray source.

A guide rail 30 may be provided on the ceiling of an examination room in which the X-ray imaging apparatus 1000 is disposed, the X-ray radiator 200 may be connected to a moving carriage 40 moving along the guide rail 30 to be moved to a position corresponding to the object P, and the moving carriage 40 and the X-ray radiator 200 may be connected to each other through a foldable post frame 50 to adjust a height of the X-ray radiator 200.

The workstation 300 may be provided with an input interface 310 including various circuitry and receiving user commands and a display 320 displaying information.

The input interface 310 may receive commands for, for example, a shooting protocol, shooting conditions, shooting timing, and position control of the X-ray radiator 200. The input interface 310 may include hardware devices such as a key, a mouse, a touch screen, and a voice recognizer.

The display 320 may display, for example, a screen image for guiding a user input, an X-ray image, a screen image indicating the status of the X-ray imaging apparatus 1000.

The controller 330 may control photographing timing, photographing conditions, etc. of the X-ray radiator 200 according to a command received from a user, and may generate a medical image using image data received from the X-ray detector 100. Additionally, the controller 330 may control the positions or postures of mounting units 14 and 24 on which the X-ray radiator 200 or the X-ray detector 100 is mounted according to the imaging protocol and the location of the object P.

The controller 330 may include a memory in which a program for performing the above-described operation and an operation to be described in greater detail below is stored, and a processor (e.g., including processing circuitry including at least one processor) for executing the stored program. The controller 330 may include a single processor or may include a plurality of processors. In the latter case, the plurality of processors may be integrated on one chip or may be physically separated from one another. The processor according to an embodiment of the disclosure may include various processing circuitry and/or multiple processors. For example, as used herein, including the claims, the term "processor" may include various processing circuitry, including at least one processor, wherein one or more of at least one processor, individually and/or collectively in a distributed manner, may be configured to perform various functions described herein. As used herein, when "a processor", "at least one processor", and "one or more processors" are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions.

The X-ray imaging apparatus 1000 may be connected to external devices (e.g., an external server 2000, a medical device 3000, and a portable terminal 4000 (e.g., a smartphone, a tablet PC, or a wearable device)) through the communication interface 340 to transmit or receive data.

The communication interface 340 may include various communication circuitry including one or more hardware devices that enable communication with an external device. For example, the communication interface 340 may include a short distance communication module, a wired communication module, and a wireless communication module.

The communication interface 340 may receive a control signal from an external device and transmit the received control signal to the controller 330 so that the controller 330 may control the X-ray imaging apparatus 1000 according to the received control signal.

By transmitting a control signal to an external device via the communication interface 340, the controller 330 may control the external device according to the control signal. For example, the external device may process data according to a control signal received from the controller 330 via the communication interface 340.

The communication interface 340 may further include an internal communication module that enables communication between the components of the X-ray imaging apparatus 1000. Because a program capable of controlling the X-ray imaging apparatus 1000 may be installed on the external device, the program may include instructions for performing some or all of the operations of the controller 330.

The program may be pre-installed on the portable terminal 4000, or a user of the portable terminal 4000 may download the program from a server providing an application and may install the downloaded program. The server providing an application may include a recording medium having the program recorded thereon.

The X-ray detector 100 may be implemented as a fixed X-ray detector fixed to a stand 20 or a table 12, or may be implemented as a mobile X-ray detector or portable X-ray detector that is detachably mounted on the mounting units 14 and 24 or may be used at any location. The mobile X-ray detector or the portable X-ray detector may be implemented in a wired type or a wireless type, according to a data transmission method and a power supply method.

The X-ray detector 100 may be included as a component of the X-ray imaging apparatus 1000 or may not be included as a component of the X-ray imaging apparatus 1000. In the latter case, the X-ray detector 100 may be registered in the X-ray imaging apparatus 1000 by a user. In addition, in both cases, the X-ray detector 100 may be connected to the controller 330 through the communication interface 340 to receive a control signal or transmit image data.

A sub-user interface 80 for providing information to the user and receiving a command from the user may be provided on one side of the X-ray radiator 200, and some or all of the functions performed by the input interface 310 and the display 320 of the workstation 300 may be performed in the sub-user interface 80.

When all or some of the components of the controller 330 and the communication interface 340 are separately provided from the workstation 300, they may be included in the sub-user interface 80 provided in the X-ray radiator 200.

Although the X-ray imaging apparatus 1000 shown in FIG. 1 is a room X-ray imaging apparatus connected to the ceiling of an examination room, the X-ray imaging apparatus 1000 may include X-ray apparatuses of various structures within a range that will be apparent to those skilled in the art, such as a C-arm type X-ray apparatus and a mobile X-ray apparatus.

Figure 2:
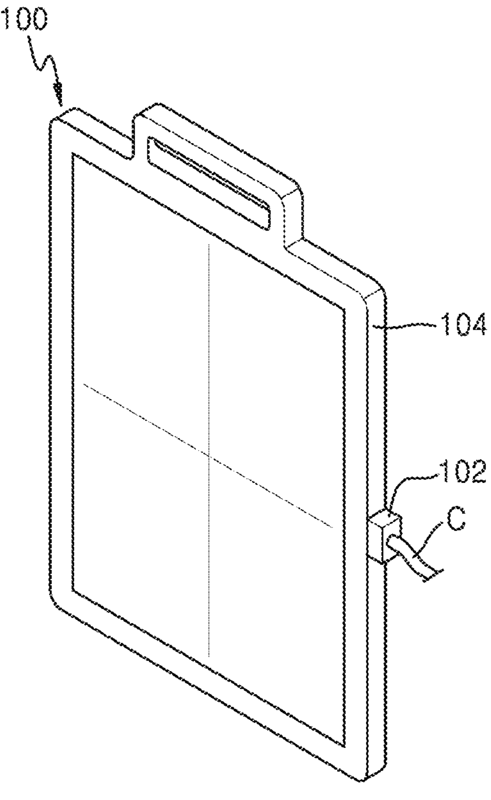
FIG. 2 is a perspective view of an X-ray detector according to various embodiments.

FIG. 2 is a perspective view illustrating an example X-ray detector 100 according to various embodiments.

Referring to FIG. 2, the X-ray detector 100 may be implemented as a mobile X-ray detector. In this case, the X-ray detector 100 may operate wirelessly by including a battery that supplies power, and, as illustrated in FIG. 2, a charging port 102 may operate by being connected to a separate power supply unit by a cable C.

A detection element detecting X-rays and converts them into image data, a memory temporarily or non-temporarily storing the image data, a communication module receiving a control signal from the X-ray imaging apparatus 1000 or transmitting the image data to the X-ray imaging apparatus 1000, and a battery may be provided inside a case 104 forming the exterior of the X-ray detector 100. In addition, image correction information of a detector and unique identification information of the X-ray detector 100 may be stored in the memory, and the stored identification information may be transmitted together with the image data during communication with the X-ray imaging apparatus 1000.

Figure 3:
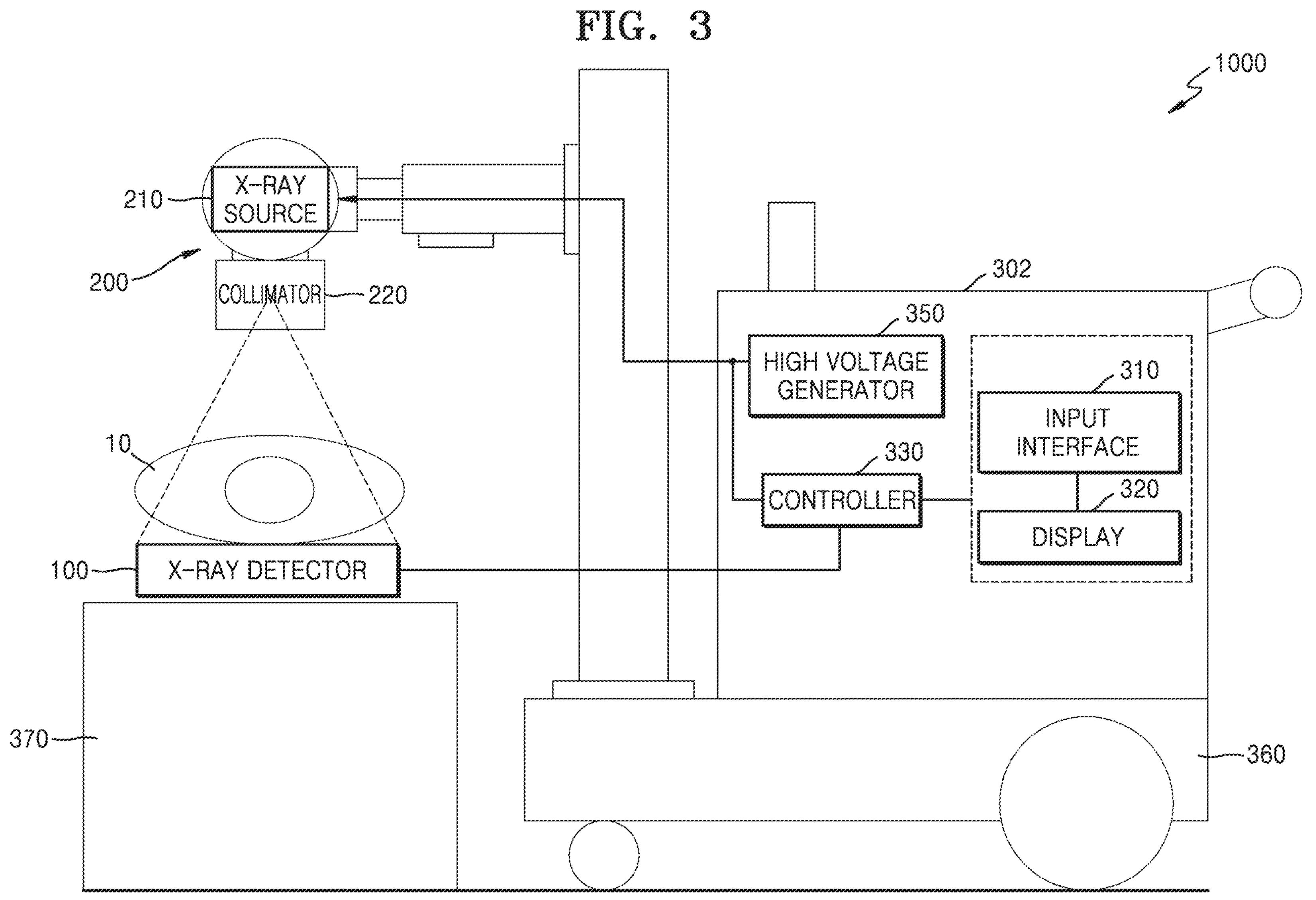
FIG. 3 is a diagram of an example configuration of an X-ray imaging apparatus including a mobile X-ray detector according to various embodiments.

FIG. 3 is a diagram illustrating an example configuration of the X-ray imaging apparatus 1000 including a mobile X-ray detector 100 according to various embodiments.

Referring to FIG. 3, the X-ray imaging apparatus 1000 may include the mobile X-ray detector 100. The mobile X-ray detector 100 is a mobile or portable X-ray detector capable of performing an X-ray photographing operation regardless of a place where the photographing operation is performed. The X-ray imaging apparatus 1000 of FIG. 3 may be an example of the X-ray imaging apparatus 1000 of FIG. 1. Components included in the X-ray imaging apparatus 1000 of FIG. 3 that are the same as those of the X-ray apparatus 1000 of FIG. 1 use the same reference numerals as those used in FIG. 1, and a redundant description thereof may not be repeated here.

Referring to FIG. 3, the X-ray imaging apparatus 300 may include the X-ray detector 100, an X-ray source 210 generating an X-ray, an X-ray radiator 200 including a collimator 220 guiding a path along which the generated X-ray is emitted and radiated by the X-ray source 210 and adjusting an irradiation region radiated by the X-ray, a main unit 302 including the controller (e.g., including processing circuitry) 330 controlling overall operations of the X-ray imaging apparatus 1000, a high voltage generator 350 generating a high voltage applied to the X-ray source 210, a transport unit 370 including a wheel for transporting the X-ray imaging apparatus 1000, and a table 370.

The main unit 302 may further include a manipulator providing a user interface for manipulating the X-ray imaging apparatus 1000. FIG. 3 illustrates the manipulator included in the main unit 302, however, the disclosure is not limited thereto. For example, as shown in FIG. 1, the input interface (e.g., including interface circuitry) 310 and the display 320 of the X-ray imaging apparatus 1000 may be provided on one side of the workstation 300 (see FIG. 1).

The X-ray imaging apparatus 1000 may be implemented not only in the above-described sealing type but also in a mobile type. Although the X-ray detector 100 in FIG. 3 is illustrated as a table type disposed on a table 390, the X-ray detector 100 may also be implemented as a stand type as a mobile type or portable type.

Figure 4:
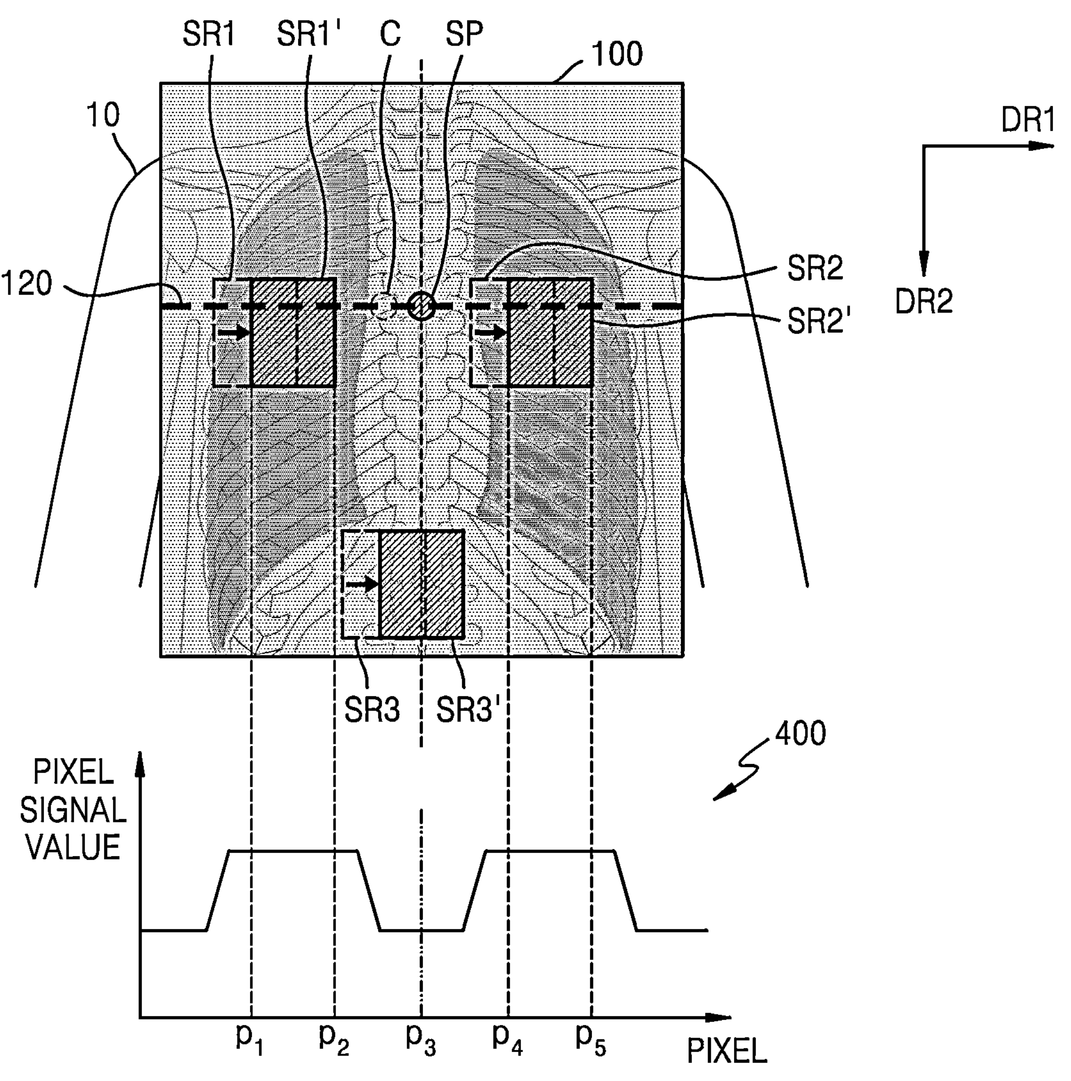
FIG. 4 is a diagram illustrating an example operation, performed by an X-ray detector, of adjusting a location of an automatic exposure control (AEC) sensing area, based on an image obtained through an AEC sensor array, according to various embodiments.

FIG. 4 is a diagram illustrating an example operation, performed by the X-ray detector 100, of adjusting respective locations of a plurality of AEC sensing areas SR1, SR2, and SR3, based on a one-dimensional (1D) image 400 obtained through an AEC sensor array 120, according to various embodiments.

Referring to FIG. 4, the X-ray detector 100 may include the AEC sensor array 120. The AEC sensor array 120 may include a plurality of AEC sensors arranged in a first direction DR1. The plurality of AEC sensors are configured to detect an X-ray that has passed through an object 10, quantify the dose of the detected X-ray as a signal value, and output the signal value. A plurality of AEC sensors according to an embodiment of the disclosure may be configured to detect visible light into which an X-ray is converted by a scintillator, convert the visible light into an electrical signal, and output a converted voltage value. According to an embodiment of the disclosure, the plurality of AEC sensors may be configured with some of a plurality of photodetection elements included in the X-ray detector 100. However, the disclosure is not limited thereto. The plurality of AEC sensors may be implemented as pixel-related AEC or AEC-related photo diode, but are not limited thereto.

Although the AEC sensor array 120 is illustrated as a single-line type sensor array structure, the AEC sensor array 120 is not limited thereto. According to an embodiment of the disclosure, the X-ray detector 100 may include a plurality of AEC sensor arrays arranged in the form of lines parallel to each other.

The X-ray detector 100 may obtain the 1D image 400 by quantifying the dose of an X-ray detected using the AEC sensor array 120 as a signal value. The 1D image 400 may include information about signal values for pixels respectively corresponding to each of the plurality of AEC sensors included in the AEC sensor array 120. Referring FIG. 4, the 1D image 400 may include a first pixel $p_1$ representing a numerical value of the dose of an X-ray detected by a first AEC sensor included in the AEC sensor array 120, a second pixel $p_2$ representing a numerical value of the dose of an X-ray detected by a second AEC sensor included in the AEC sensor array 120, a third pixel $p_3$ representing a numerical value of the dose of an X-ray detected by a third AEC sensor included in the AEC sensor array 120, a fourth pixel $p_4$ representing a numerical value of the dose of an X-ray detected by a fourth AEC sensor included in the AEC sensor array 120, and a fifth pixel $p_5$ representing a numerical value of the dose of an X-ray detected by a fifth AEC sensor included in the AEC sensor array 120. The first through fifth pixels $p_1$ through $p_5$ are only for convenience of explanation, and the pixels included in the 1D image 400 are not limited to the five pixels shown in FIG. 4.

The X-ray detector 100 may identify a symmetric point SP from the 1D image 400, based on a signal value for each pixel of the 1D image 400. The 'symmetric point SP' may be a central point about which the respective signal values of the plurality of pixels included in the 1D image 400 are bilaterally symmetrical. According to an embodiment of the disclosure, the X-ray detector 100 may identify the symmetric point SP by calculating an average value of differences between a signal value of each of the plurality of pixels included in the 1D image 400 and signal values of the other pixels spaced apart from each of the plurality of pixels and searching for a minimum value from the calculated average values. Referring to FIG. 4, the X-ray detector 100 may calculate an average value of differences between a signal value of each of the plurality of pixels $p_1$ through $p_5$ and signal values of the other pixels spaced apart therefrom, and search for a pixel ($p_3$ illustrated in FIG. 4) with a minimum value among the calculated average values. The X-ray detector 100 may identify, as the symmetric point SP, a location of the found third pixel $p_3$ on a photographing surface of the X-ray detector 100.

According to an embodiment of the disclosure, the X-ray detector 100 may detect a plurality of pixels corresponding to edge points in the 1D image 400, obtain an edge point pair among the detected plurality of pixels, and identify a center point of the obtained edge point pair as the symmetric point SP.

The X-ray detector 100 may adjust the locations of the plurality of AEC sensing areas SR1, SR2 and SR3 relative to the identified symmetric point SP. The AEC sensing area may be set to perform an AEC function of detecting the dose of X-rays passing through an object on an imaging surface of an X-ray detector, and blocking X-rays when the detected dose of X-rays exceeds a preset threshold. According to an embodiment of the disclosure, the plurality of AEC sensing areas SR1, SR2 and SR3 may be areas pre-set by an input received from a user (e.g., a radiologist or a doctor), or areas determined according to an initial default. According to an embodiment of the disclosure, the X-ray detector 100 may obtain location information of a center point C between a first AEC sensing area SR1 and a second AEC sensing area SR2 disposed on the left and right sides of the identified symmetric point SP, and change the locations of the first AEC sensing area SR1 and the second AEC sensing area SR2 so that the location of the center point C coincides with the location of the symmetric point SP. Referring to FIG. 4, the X-ray detector 100 may change the location of the first AEC sensing area SR1 to SR1' and change the location of the second AEC sensing area SR2 to SR2'. According to an embodiment of the disclosure, the X-ray detector 100 may change the location of a third AEC sensing area SR3 to the same displacement value as respective displacement values of the first AEC sensing area SR1 and the second AEC sensing area SR2. Referring to FIG. 4, the X-ray detector 100 may change the location of the third AEC sensing area SR3 to SR3'.

A general mobile X-ray detector including an AEC sensor is located at the back of a patient during X-ray imaging, so a user (e.g., a radiologist or a doctor) should check the outline of the X-ray detector and a patient's anatomy by eyes. Therefore, the mobile X-ray detector may be inaccurately positioned, and alignment between X-ray source-patient-AEC sensor-X-ray detector may not be achieved. When the accuracy of the alignment between the X-ray source-patient-AEC sensor-X-ray detector is low, the possibility of malfunction increases, and, when the degree of misalignment is large, there is a risk of accidents such as X-ray over-radiation. For example, in the case of mobile X-ray detectors, an X-ray detector located behind a patient is not visible, prediction of the amount of X-ray radiation may be failed, and an X-ray image with an image quality sufficient for reading may not be obtained.

To address this problem, a method of attaching a location detection sensor to an AEC sensor, identifying a relative location of the AEC sensor with respect to an X-ray source, and performing pre-notification or post-correction according to an alignment state may be considered. However, the location detection sensor is an expensive component part, and has limitations that precision and reliability are not high.

The disclosure provides the X-ray detector 100 automatically correcting an AEC sensing area, based on an image obtained using the AEC sensor array 120, and a method of operating the X-ray detector 100.

The X-ray detector 100 according to an embodiment of the disclosure may obtain the 1D image 400 representing a numerical value of the dose of an X-ray transmitted through the object 10 using the AEC sensor array 120, identify the symmetric point SP from the 1D image 400, and adjust the respective locations of the plurality of AEC sensing areas SR1, SR2, and SR3 relative to the symmetric point SP, thereby preventing and/or reducing X-ray over-radiation onto a patient and providing a high-quality X-ray image. In addition, the X-ray detector 100 according to an embodiment of the disclosure may prevent and/or reduce retake due to failure to predict the amount of X-ray radiation, and reduce the average dose of X-rays radiated during photographing.

Figure 5:
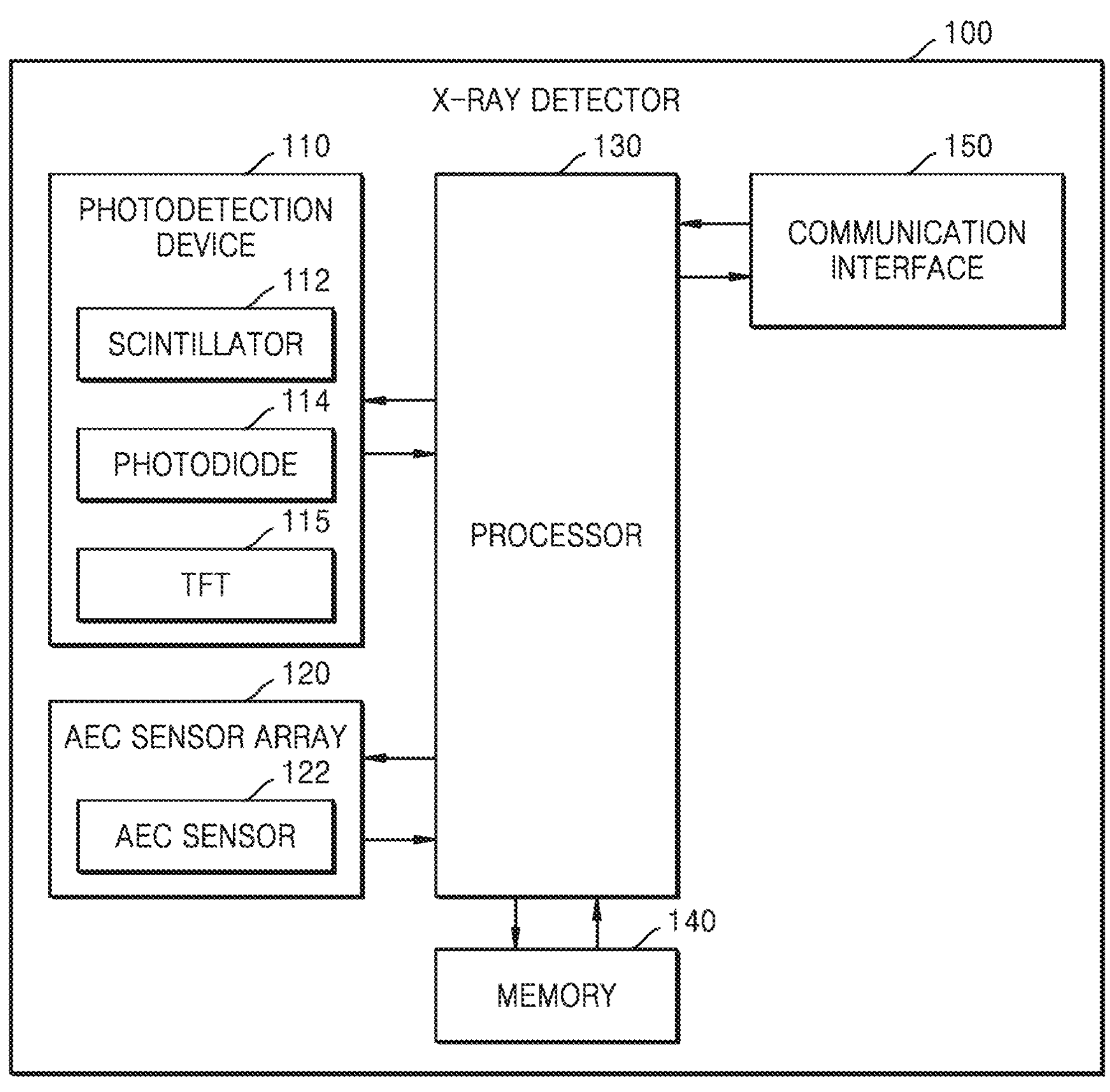
FIG. 5 is a block diagram illustrating an example configuration of an X-ray detector according to various embodiments.

FIG. 5 is a block diagram illustrating an example configuration of the X-ray detector 100 according to various embodiments.

Referring to FIG. 5, the X-ray detector 100 may include a photodetection element (e.g., including various circuitry) 110, an AEC sensor array (e.g., including at least one AEC sensor) 120, a processor (e.g., including processing circuitry) 130, a memory 140, and a communication interface (e.g., including communication circuitry) 150. The components shown in FIG. 5 are merely an example, and the components included in the X-ray detector 100 are not limited to those shown in FIG. 5. The X-ray detector 100 may not include some of the components illustrated in FIG. 5, and may further include components not illustrated in FIG. 5. For example, when the X-ray detector 100 is implemented as a mobile X-ray detector, the X-ray detector 100 may further include a battery.

The photodetection element 110 and the AEC sensor array 120 will be described in greater detail below with reference to FIGS. 5 and 6.

The photodetection element 110 may include various circuitry and detect an X-ray radiated to an object by the X-ray radiator 200 of FIG. 1 (for example, an X-ray tube) and transmitted through the object, and generate an electrical signal corresponding to the intensity of the detected X-ray. The photodetection element 110 may be provided in plurality. The plurality of photodetection elements 110 may include pixels arranged in a two-dimensional (2D) form of N×M. The photodetection element 110 may include a scintillator 112, a photodiode 114, and a TFT 116.

The scintillator 112 may include an X-ray sensitive material and is configured to convert the X-ray transmitted through the object into visible light. The scintillator 112 may react with the X-ray incident on the X-ray detector 100 to emit photons having a wavelength (e.g., a wavelength of 300 to 800 nm) in a visible light region. According to an embodiment of the disclosure, when the photodetection element 110 performs a direct type detection method of directly converting an X-ray into electric charge and detecting the electrical charge, the scintillator 112 may be replaced with a photon counting detector. The scintillator 112 may be made of, for example, gadolinium oxysulfide (GoS, Gadox), cesium iodide (CsI), or amorphous silicon (a-Si), but is not limited thereto.

The photodiode 114 is configured to receive the photons emitted by the scintillator 112 and convert the photons into an electrical signal. The photodiode 114 may provide the electrical signal to the processor 130. The photodiode 114 may be formed as a substrate in which a plurality of pixels are arranged in a 2D form of N×M. A plurality of pixels formed on the substrate of the photodiode 114 may include a photoelectric convertor configured to generate electric charges according to visible light and accumulate the generated electric charges, and a switching element that is connected to the photoelectric convertor and configured to detect the electric charges accumulated in the photoelectric convertor. According to an embodiment, the photoelectric convertor may be configured with a PIN diode, but is not limited thereto. According to an embodiment of the disclosure, the switching device may be configured with the TFT 116. However, the disclosure is not limited thereto.

The AEC sensor array 120 may include at least one or a plurality of AEC sensors 122. The AEC sensor array 120 may be formed in a line-shaped array structure in which the plurality of AEC sensors 122 are arranged in a first direction.

According to an embodiment of the disclosure, the AEC sensor array 120 may include a plurality of sensor arrays arranged to be parallel to each other in the first direction. A structure of a plurality of AEC sensor arrays 120 will be described in detail with reference to FIG. 7B.

The plurality of AEC sensors 122 are configured to detect the X-ray transmitted through the object, quantify the dose of the detected X-ray as a signal value, and output the signal value. The plurality of AEC sensors 122 may be configured as an integrated sensor included in the X-ray detector 100. The plurality of AEC sensors 122 according to an embodiment of the disclosure may be configured with a portion of the plurality of photodetection elements 110, and may be formed in the same structure as the plurality of photodetection elements 110. For example, similar to the photodetection element 110, the plurality of AEC sensors 122 may include the scintillator 112, the photodiode 114, and the TFT 116. The plurality of AEC sensors 122 may detect visible light converted from the X-ray by a scintillator, convert the visible light into an electrical signal through a photodiode, and output a converted voltage value. The plurality of AEC sensors 122 may be implemented as pixel-related AEC or AEC-related photo diode, but are not limited thereto.

Respective structures and respective operations of the photodetection element 110 and the AEC sensor array 120 will be described in greater detail below with reference to FIG. 6.

The processor 130 may include various processing circuitry and execute a program code or one or more instructions stored in the memory 140. The processor 130 may include hardware components that perform arithmetic, logic, input/output operations and signal processing. The processor 130 may include, but is not limited to, at least one of a central processing unit, a microprocessor, a graphics processing unit, application specific integrated circuits (ASICs), digital signal processors (DSPs), digital signal processing devices (DSPDs), programmable logic devices (PLDs), or field programmable gate arrays (fPGAs). The processor 130 according to an embodiment of the disclosure may include various processing circuitry and/or multiple processors. For example, as used herein, including the claims, the term "processor" may include various processing circuitry, including at least one processor, wherein one or more of at least one processor, individually and/or collectively in a distributed manner, may be configured to perform various functions described herein. As used herein, when "a processor", "at least one processor", and "one or more processors" are described as being configured to perform numerous functions, these terms cover situations, for example and without limitation, in which one processor performs some of recited functions and another processor(s) performs other of recited functions, and also situations in which a single processor may perform all recited functions. Additionally, the at least one processor may include a combination of processors performing various of the recited/disclosed functions, e.g., in a distributed manner. At least one processor may execute program instructions to achieve or perform various functions.

The processor 130 is illustrated as a single element in FIG. 5, but the disclosure is not limited thereto. According to an embodiment, the processor 130 may be provided as one or in plurality.

According to an embodiment of the disclosure, the processor 130 may include an artificial intelligence (AI) processor that perform AI learning. In this case, the AI processor may perform inference using an AI model. The AI processor may be manufactured in the form of an dedicated hardware chip for AI (for example, a neural processing unit (NPU)), or may be manufactured as a part of an existing general-purpose processor (for example, a central processing unit (CPU) or an application processor) or a graphic-dedicated processor (for example, a GPU).

The memory 140 may include at least one type of storage medium from among, for example, a flash memory type storage medium, a hard disk type storage medium, a multimedia card micro type storage medium, a card type memory (for example, SD or XD memory), a random access memory (RAM), a static RAM (SRAM), a read-only memory (ROM), an electrically erasable programmable ROM (EEPROM), a programmable ROM (PROM), and an optical disk.

The memory 140 may store instructions or program codes for performing functions or operations of the X-ray detector 100. According to an embodiment, at least one of instructions, an algorithm, a data structure, program code, or an application program readable by the processor 130 may be stored in the memory 140. The instructions, algorithm, data structure, and program code stored in the memory 140 may be implemented in, for example, programming or scripting languages such as C, C++, Java, assembler, and the like.

According to an embodiment below, the processor 130 may be implemented by executing the instructions or program codes of a program stored in the memory 140.

The processor 130 may obtain a 1D image by quantifying the dose of an X-ray detected by the AEC sensor array 120 as a signal value. The 1D image may include information about signal values for pixels respectively corresponding to the plurality of AEC sensors 122 included in the AEC sensor array 120. According to an embodiment of the disclosure, the processor 130 may obtain a 1D image in real time by reading out an electrical signal representing the dose of X-rays detected by the plurality of AEC sensors 122 at a preset sampling rate. For example, the processor 130 may obtain a 1D image in real time by performing sampling once during a time of 100 μs or less. However, the time of 100 μs is merely an example, and the sampling time is not limited thereto.

The processor 130 may identify a symmetric point from the 1D image, based on a signal value for each pixel of the 1D image. The 'symmetric point' may be a central point about which the respective signal values of the plurality of pixels included in the 1D image are bilaterally symmetrical. The processor 130 may identify the symmetric point by detecting a pixel pair with a minimum difference value between corresponding pixels with respect to an initial symmetrical point in the 1D image, and obtaining the location of the center point of the detected pixel pair. According to an embodiment of the disclosure, the processor 130 may identify the symmetric point by calculating an average value of the differences between a signal value of each of the plurality of pixels included in the 1D image and respective signal values of the other left and right pixels, searching for a minimum value from the calculated average values, and moving the location of an initial symmetric point based on a location of a center point of the left and right pixels that has the searched minimum value. An embodiment in which the processor 130 identifies the symmetric point using a difference between the signal values of the left and right pixels will be described in detail with reference to FIGS. 9 and 10.

According to an embodiment of the disclosure, the processor 130 may detect a plurality of pixels corresponding to edge points from among the plurality of pixels included in the 1D image, obtain an edge point pair among the detected plurality of pixels, and identify a center point of the obtained edge point pair as the symmetric point. An embodiment in which the processor 130 identifies the symmetric point by detecting a plurality of pixels corresponding to edge points will be described in detail with reference to FIGS. 11 and 12.

When the AEC sensor array 120 includes a plurality of sensor arrays arranged in parallel, the processor 130 may sum pixel signal values of the 1D image respectively obtained through the plurality of AEC sensor arrays 120 according to corresponding pixels, and may identify the symmetric point, based on the summed pixel signal value. An embodiment in which the processor 130 identifies the symmetric point from a sum of the pixel signal values of the 1D image respectively obtained through the plurality of AEC sensor arrays 120 will be described in greater detail below with reference to FIG. 13.

The processor 130 may adjust the locations of the plurality of AEC sensing areas relative to the identified symmetric point. The AEC sensing area may be set to perform an AEC function of detecting the dose of X-rays passing through an object on an imaging surface of an X-ray detector, and blocking X-rays when the detected dose of X-rays exceeds a preset threshold. According to an embodiment of the disclosure, the plurality of AEC sensing areas may be areas pre-set by an input received from a user (e.g., a radiologist or a doctor). However, the disclosure is not limited thereto, and the plurality of AEC sensing areas may be initial default areas. According to an embodiment of the disclosure, the processor 130 may obtain location information of a center point of the plurality of AEC sensing areas arranged on the left and right sides of the identified symmetric point, and may change the locations of the plurality of AEC sensing areas such that the location of the center point is consistent with the location of the symmetric point. An embodiment in which the processor 130 adjusts the locations of the plurality of AEC sensing areas relative to the symmetric point will be described in detail with reference to FIGS. 14 and 15.

As the 1D image is generated in real time, the processor 130 may identify the symmetric point in real time, and may adjust the locations of the plurality of AEC sensing areas.

The processor 130 may measure a voltage signal representing the dose of the X-rays detected by a plurality of AEC sensors 122 disposed in the plurality of AEC sensing areas among the plurality of AEC sensors 122 included in the AEC sensor array 120, and may monitor the voltage signal in real time. The processor 130 may compare a value of the voltage signal output by the plurality of AEC sensors 122 disposed in the plurality of AEC sensing areas 122 with a preset cut-off threshold, and may generate an X-ray cut-off signal when the value of the voltage signal exceeds the cut-off threshold. The processor 130 may transmit the X-ray cut-off signal to an X-ray source controller in the workstation 300 (see FIG. 1) or the X-ray radiator 200 (see FIGS. 1 and 3) through the communication interface 150.

As X-ray radiation by the X-ray radiator 200 ends, the processor 130 may obtain X-ray image data by performing a read-out operation. The processor 130 may generate X-ray image data about the object using the electrical signal obtained by the photodetection element 110. The processor 130 according to an embodiment of the disclosure may include an amplifier circuit amplifying an analog signal obtained by the photodiode 114 of the photodetection element 110, and an analog-to-digital conversion (ADC) chip converting the amplified analog signal into a digital signal. The read-out operation of the X-ray detector 100 may be well known to one of ordinary skill in the art to which the disclosure pertains, and thus a detailed description thereof may not be provided here.

The communication interface 150 may include various communication circuitry and is configured to perform data communication with the workstation 300 (see FIG. 1) or the X-ray radiator 200 (see FIGS. 1 and 3) through a wired or wireless communication network. According to an embodiment, the communication interface 150 may transmit the X-ray cut-off signal to the workstation 300 or the X-ray radiator 200, under a control by the processor 130.

The communication interface 150 may perform data communication with the workstation 300 or the X-ray irradiation unit 200 using, for example, wired data communication such as a communication cable or a wired LAN. However, the disclosure is not limited thereto, and, when the X-ray detector 100 is implemented as a mobile detector, the communication interface 150 may be configured to perform data communication using at least one wireless data communication network from among, for example, a wired LAN, a wireless LAN, Wi-Fi, Bluetooth, Zigbee, Wi-Fi Direct (WFD), Bluetooth Low Energy (BLE), Wireless Broadband Internet (Wibro), World Interoperability for Microwave Access (WiMAX), a shared wireless access protocol (SWAP), Wireless Gigabit Alliance (WiGig), and RF communication.

Figure 6:
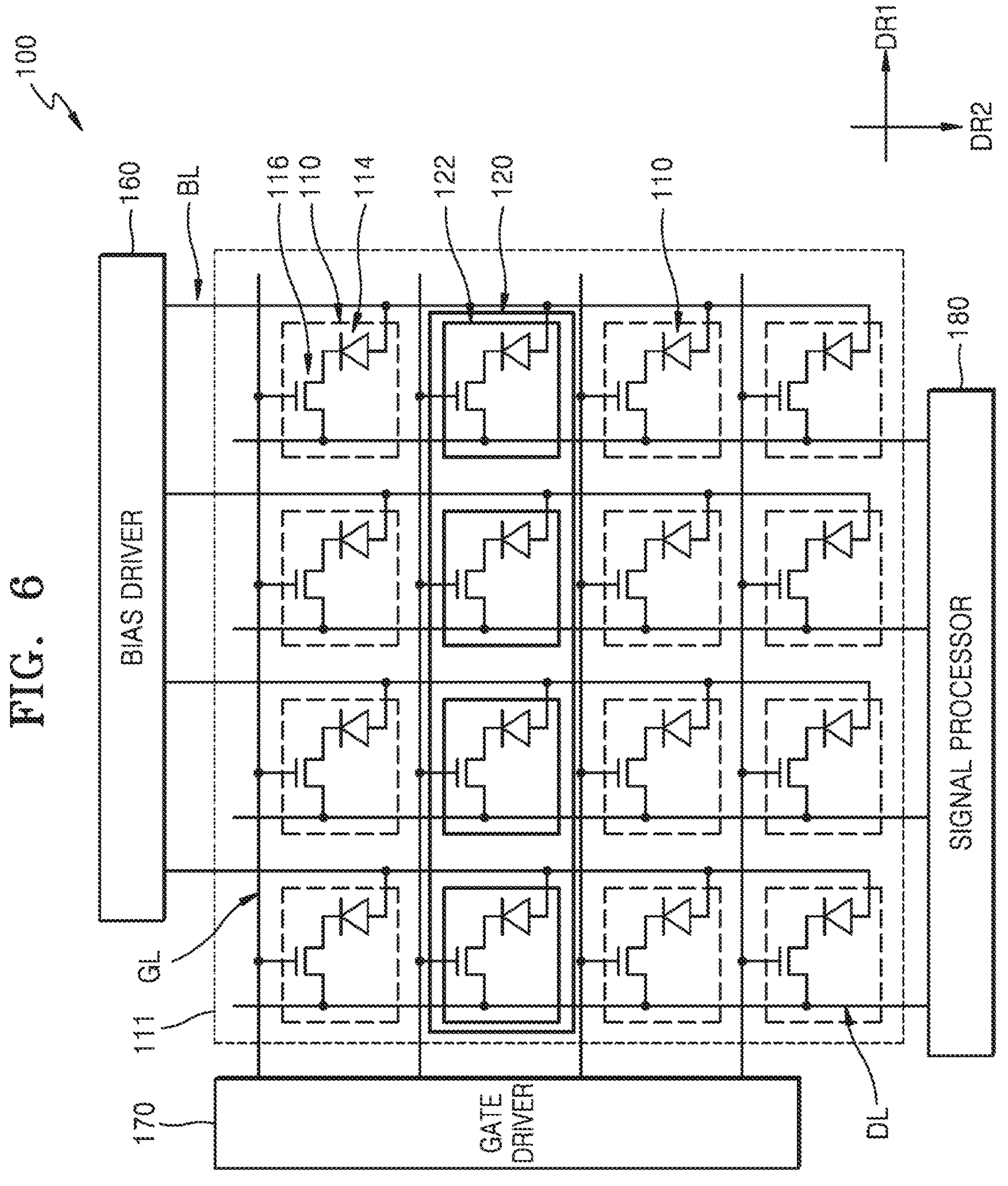
FIG. 6 is a diagram illustrating an example structure of a photodetection element and an AEC sensor array among the components of an X-ray detector according to various embodiments.

FIG. 6 is a diagram illustrating an example structure and configuration of the photodetection element 110 and the AEC sensor array 120 among the components of the X-ray detector 100 according to various embodiments.

The X-ray detector 100 of FIG. 6 may be an example of the X-ray detector 100 of FIG. 5. The X-ray detector 100 of FIG. 6 may be an indirect type detector.

Referring to FIG. 6, the X-ray detector 100 may include a scintillator (not shown), the photodetection element (e.g., including circuitry) 110, a photodetection substrate 111, the AEC sensor array (e.g., including at least one AEC sensor) 120 a bias driver 160, a gate driver 170, and a signal processor (e.g., including signal processing circuitry) 180.

The scintillator 112 (e.g., see FIG. 5) may receive an X-ray radiated from an X-ray source and convert the X-ray into visible light. The scintillator 112 may the same as or similar to the scintillator (not shown) of FIG. 6, and thus a redundant description thereof may not be repeated here.

The photodetection substrate 111 receives the light from the scintillator and converts the light into an electrical signal. The photodetection substrate 111 may include gate lines GL, data lines DL, a plurality of photodiodes 114, a plurality of TFTs 116, and bias lines BL.

The gate lines GL may be formed in a first direction DR1, and the data lines DL may be formed in a second direction DR2 intersecting the first direction DR1. The first direction DR1 and the second direction DR2 may intersect perpendicularly to each other. Referring to FIG. 6, the X-ray detector 100 may include four gate lines GL and four data lines DL. However, the numbers of gate lines GL and data lines DL included in the X-ray detector 100 of the disclosure are not limited to the above example.

The plurality of TFTs 116 may be arranged in a matrix form in the first and second directions DR1 and DR2. Each of the TFTs 116 may be electrically connected to one of the gate lines GL and one of the data lines DL. A gate of the TFT 116 may be electrically connected to the gate line GL, and a source of the TFT 116 may be electrically connected to the data line DL. Referring to FIG. 6, the X-ray detector 100 may include sixteen TFTs 116 in a 4×4 arrangement. However, the disclosure is not limited thereto, and the number of TFTs 116 is not limited to the above example.

The photodiodes 114 may be arranged in a matrix form in the first and second directions DR1 and DR2 so as to respectively correspond to the TFTs 116. Each of the plurality of photodiodes 114 may be electrically connected to one of the plurality of TFTs 116. An N-side electrode of the photodiode 114 may be electrically connected to a drain of the TFT 116. Each of the plurality of photodiodes 114 may receive a bias voltage from the bias driver 160 through the bias line BL. Due to the application of the bias voltage, an electric field may be generated within a semiconductor layer of the photodiode 114, a charge (electron-hole pair) generated within the semiconductor layer due to photoelectric conversion may move to upper and lower electrodes, one of which having a positive (+) polarity and the other having a negative (−) polarity, and charges may be accumulated in the photodiode 114. Referring to FIG. 6, the X-ray detector 100 may include sixteen photodiodes 114 in a 4×4 arrangement. However, the disclosure is not limited thereto, and the number of photodiodes 114 is not limited to the above example.

The bias lines BL may be electrically connected to the plurality of photodiodes 114. Each of the bias lines BL may be electrically connected to P-side electrodes of each of the plurality of photodiodes 114 arranged in one direction. For example, the bias lines BL may be formed to be substantially parallel to the second direction DR2 and thus may be electrically connected to the plurality of photodiodes 114. According to an embodiment of the disclosure, the bias lines BL may be formed to be substantially parallel to the first direction DR1 and thus may be electrically connected to the photodiodes 114. Referring to FIG. 6, the X-ray detector 100 may include four bias lines BL formed in the second direction DR2. However, the disclosure is not limited thereto, and the number of bias lines BL is not limited to the above example.

The bias driver 160 may be electrically connected to the bias lines BL and thus may apply a driving voltage to the bias lines BL. The bias driver 160 may selectively apply a reverse bias voltage or a forward bias voltage to the photodiodes 114. A reference voltage may be applied to N-side electrodes of the photodiodes 114. The reference voltage may be applied via the signal processor 180. The bias driver 160 may apply a lower voltage than the reference voltage to the P-side electrodes of the photodiodes 114 in order to apply a reverse bias voltage to the photodiodes 114. The bias driver 160 may apply a higher voltage than the reference voltage to the P-side electrodes of the photodiodes 114 in order to apply a forward bias voltage to the photodiodes 114.

The gate driver 170 may be electrically connected to the gate lines GL and thus may apply gate signals to the gate lines GL. For example, when the gate signals are applied to the gate lines GL, the TFTs 116 may be turned on by the gate signals. On the other hand, when the gate signals are not applied to the gate lines GL, the TFTs 116 may be turned off.

The signal processor 180 is electrically connected to the data lines DL. When the light received by the photodetection substrate 111 is converted into the electrical signal, the electrical signal may be read out by the signal processor 180 via the data lines DL.

During the operation of the X-ray detector 100, the bias driver 160 may apply the reverse bias voltage to the photodiodes 114.

While the plurality of TFTs 116 are being turned off, each of the plurality of photodiodes 114 may receive the light from the scintillator and generate electron-hole pairs to accumulate electric charges. The number of electric charges accumulated in each of the photodiodes 114 may correspond to the number of X-rays.

Then, the gate driver 170 may sequentially apply the gate signals to the gate lines GL in the second direction DR2. When a gate signal is applied to a gate line GL and thus TFTs 116 are turned on, photocurrents may flow into the signal processor 180 via a data line DL due to the electric charges accumulated in the photodiodes 114.

The signal processor 180 may convert the received photocurrents into image data. The signal processor 180 may output the image data to the outside. The image data may be in the form of an analog signal or a digital signal corresponding to the photocurrents.

Some of the plurality of photodetection elements 110 may be AEC sensors 122. Referring to FIG. 6, four photodetection elements 110 arranged in the first direction DR1 in a second row among the plurality of photodetection elements 110 may operate as AEC sensors 122. The AEC sensors 122 may comprise an AEC sensor array 120.

According to an embodiment of the disclosure, the gate driver 170 may apply a gate signal at a high sampling rate through a gate line GL connected to a plurality of AEC sensors 122 included in an AEC sensor array 120. The gate driver 170 may apply a gate signal to the plurality of AEC sensors 122 at a higher sampling rate than the gate signal applied to the plurality of photodetection elements 110. When the gate signal is applied through the gate line GL and thus TFTs 116 respectively included in the plurality of AEC sensors 122 are turned on, photocurrents may flow into the signal processor 180 via a data line DL due to the electric charges accumulated in the photodiodes 114. The signal processor 180 may obtain image data by reading out the photocurrents output by the plurality of AEC sensors 122 at a high sampling rate. According to an embodiment of the disclosure, the signal processor 180 may read out photocurrents output by the plurality of AEC sensors 122 at a higher sampling rate than a sampling rate at which the photocurrents output by the plurality of photodetection elements 110 are read out.

The signal processor 180 may convert a photocurrent value proportional to the dose of X-rays detected by the plurality of AEC sensors 122 into image data by quantifying the photocurrent value, and may output the image data. The processor 130 (see FIG. 5) may obtain the 1D image using the image data output by the signal processor 180.

In FIG. 6, the gate driver 170 applies gate signals not only to the plurality of photodetection elements 110 but also to the plurality of AEC sensors 122 included in the AEC sensor array 120. However, the disclosure is not limited to that shown in FIG. 6. According to an embodiment of the disclosure, a gate signal may be applied to the plurality of AEC sensors 122 included in the AEC sensor array 120 by a gate driver other than the gate driver 170.

In FIG. 6, the signal processor 180 obtains the 1D image using signal values output by not only the plurality of photodetection elements 110 but also by the plurality of AEC sensors 122 included in the AEC sensor array 120. However, the disclosure is not limited to that shown in FIG. 6. According to an embodiment of the disclosure, the signal values output by the plurality of AEC sensors 122 included in the AEC sensor array 120 may be output to a signal processor other than the signal processor 180, and a 1D image may be obtained by the other signal processor.

In an embodiment, switching devices such as TFTs 116 may not be disposed in the plurality of AEC sensors 122 included in the AEC sensor array 120, and the plurality of AEC sensors 122 may be short-circuited with lines, so that signal charges generated by the plurality of AEC sensors 122 may be immediately transferred to the processor 130. In this case, when X-rays are detected, the plurality of AEC sensors 122 may directly transmit signal charges to the processor 130 through lines.

Figure 7A:
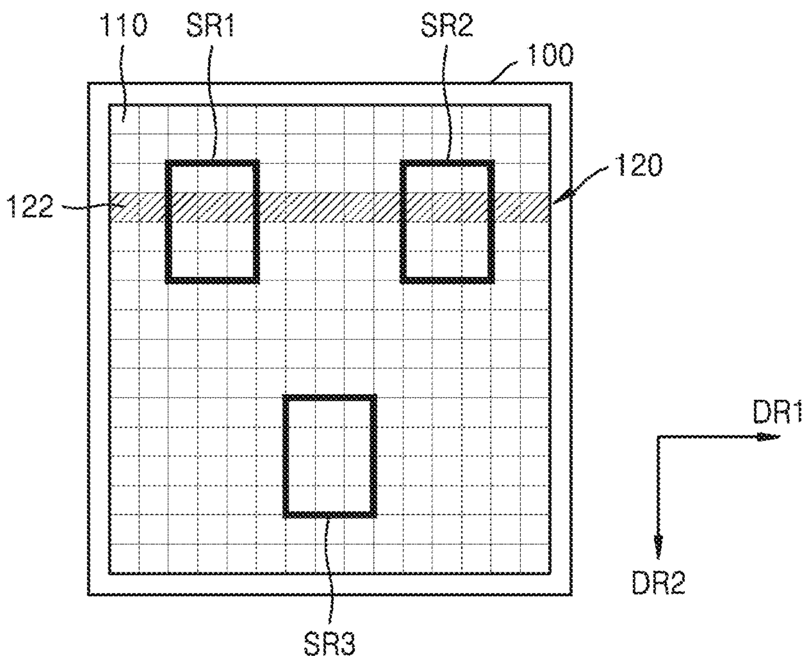
FIG. 7A is a diagram illustrating an example layout structure of an AEC sensor array of an X-ray detector according to various embodiments.

FIG. 7A is a diagram illustrating an example layout configuration of an AEC sensor array 120 of the X-ray detector 100 according to various embodiments.

Referring to FIG. 7A, the X-ray detector 100 may include a plurality of photodetection elements 110 and a plurality of AEC sensors 122. The plurality of AEC sensors 122 may be formed in the same structure as the plurality of photodetection elements 110. According to an embodiment of the disclosure, the plurality of AEC sensors 122 may be configured with some of the plurality of photodetection elements. However, the disclosure is not limited thereto. Because the plurality of AEC sensors 122 are the same as those described above with reference to FIGS. 5 and 6, a redundant description thereof may not be repeated here.

The AEC sensor array 120 may include a plurality of AEC sensors 122 arranged in the first direction DR1.

The plurality of AEC sensing areas SR1, SR2, and SR3 may be included on the imaging surface of the X-ray detector 100. The plurality of AEC sensing areas SR1, SR2, and SR3 are areas set to perform an AEC function. When the dose of X-rays detected by photodetection elements 110 or AEC sensors 122 arranged in the plurality of AEC sensing areas SR1, SR2, and SR3 exceeds a preset cut-off threshold, an X-ray cut-off signal may be transmitted to the X-ray radiator 200 (see FIGS. 1 and 3). According to an embodiment of the disclosure, the plurality of AEC sensing areas SR1, SR2, and SR3 may be areas pre-set by an input received from a user (e.g., a radiologist or a doctor). However, the disclosure is not limited thereto, and the plurality of AEC sensing areas SR1, SR2, and SR3 may be initial default areas.

Although FIG. 7A illustrates the X-ray detector 100 including three AEC sensing areas SR1, SR2, and SR3, the AEC sensing areas SR1, SR2, and SR3 according to the disclosure are not limited to three. According to an embodiment of the disclosure, the AEC sensing area may be provided as one or in plurality.

At least one AEC sensor 122 among the plurality of AEC sensors 122 included in the AEC sensor array 120 may be disposed at locations in the plurality of AEC sensing areas SR1, SR2, and SR3. Referring to FIG. 7A, at least one AEC sensor 122 among the plurality of AEC sensors 122 included in the AEC sensor array 120 may be disposed at locations in the first AEC sensing area SR1 and the second AEC sensing area SR2. The at least one AEC sensor 122 disposed at locations in the first AEC sensing area SR1 and the second AEC sensing area SR2 may detect X-rays incident on the first AEC sensing area SR1 and the second AEC sensing area SR2, convert the dose of the detected X-rays into an electrical signal, and quantify and output the electrical signal.

Figure 7B:
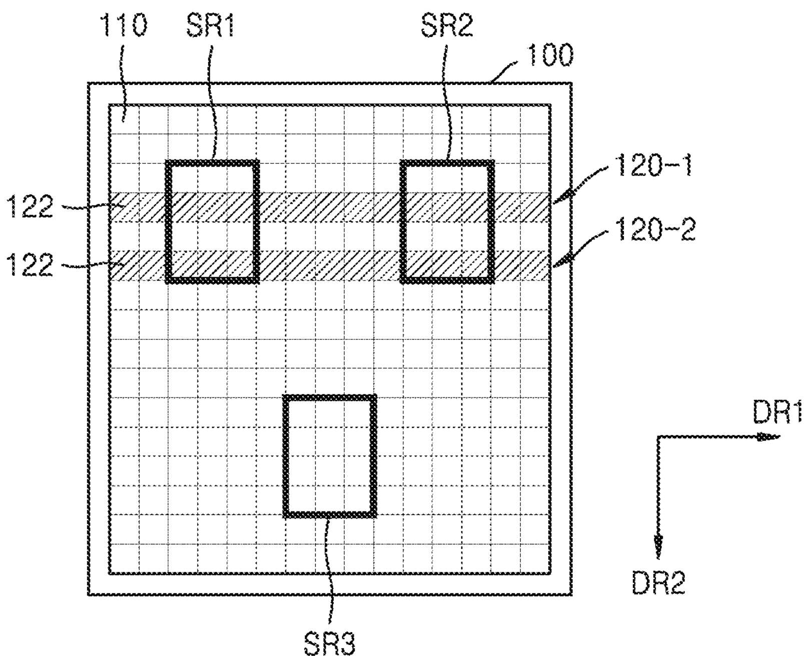
FIG. 7B is a diagram illustrating an example layout structure of an AEC sensor array of an X-ray detector according to various embodiments.

FIG. 7B is a diagram illustrating an example layout configuration of a plurality of AEC sensor arrays 120-1 and 120-2 of the X-ray detector 100 according to various embodiments.

Because the X-ray detector 100 according to FIG. 7B is the same as or similar to the X-ray detector 100 shown in FIG. 7A except that the X-ray detector 100 of FIG. 7B includes the plurality of AEC sensor arrays 120-1 and 120-2, redundant descriptions of the plurality of photodetection elements 110, the plurality of AEC sensors 120, and the plurality of AEC sensing areas SR1, SR2, and SR3 may not be repeated here.

Referring to FIG. 7B, the X-ray detector 100 may include a first AEC sensor array 120-1 and a second AEC sensor array 120-2. The first AEC sensor array 120-1 and the second AEC sensor array 120-2 may each be formed in a form of lines parallel to each other along the first direction DR1, and may be arranged to be spaced apart from each other by a predetermined distance.

Each of the first AEC sensor array 120-1 and the second AEC sensor array 120-2 may include a plurality of AEC sensors 122. Some of the plurality of AEC sensors 122 included in each of the first AEC sensor array 120-1 and the second AEC sensor array 120-2 may be disposed to be located in the plurality of AEC sensing areas SR1, SR2, and SR3. Referring to FIG. 7B, at least one AEC sensor 122 among the plurality of AEC sensors 122 included in the first AEC sensor array 120-1 may be disposed within the first AEC sensing area SR1 and the second AEC sensing area SR2. Likewise, at least one AEC sensor 122 among the plurality of AEC sensors 122 included in the second AEC sensor array 120-2 may be disposed within the first AEC sensing area SR1 and the second AEC sensing area SR2.

The at least one AEC sensor 122 disposed at locations in the first AEC sensing area SR1 and the second AEC sensing area SR2 may detect X-rays incident on the first AEC sensing area SR1 and the second AEC sensing area SR2, convert the dose of the detected X-rays into an electrical signal, and quantify and output the electrical signal.

Figure 8:
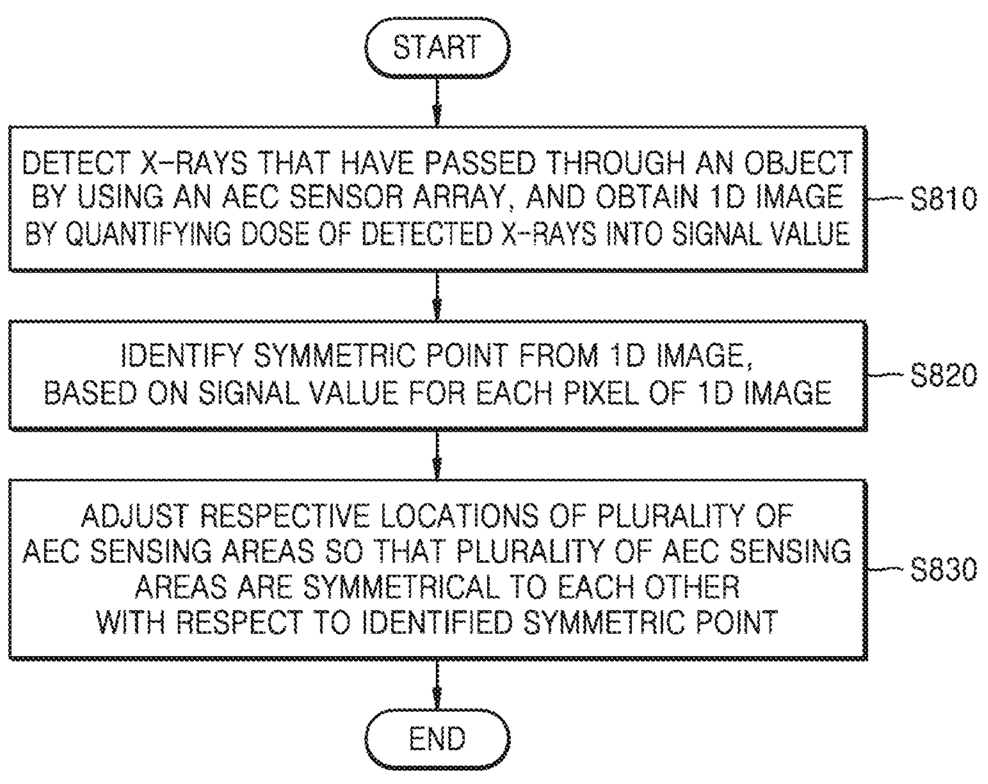
FIG. 8 is a flowchart illustrating an example method of operating an X-ray detector, according to various embodiments.

FIG. 8 is a flowchart illustrating an example method of operating the X-ray detector 100, according to various embodiments.

In operation S810, the X-ray detector 100 may detect X-rays that have passed through an object, using an AEC sensor array, and obtains a 1D image by quantifying the dose of the detected X-rays into a signal value. The 1D image may include information about signal values for pixels respectively corresponding to the plurality of AEC sensors 122 (see FIGS. 5 and 6) included in the AEC sensor array 120 (see FIGS. 5 and 6). According to an embodiment of the disclosure, the X-ray detector 100 may obtain a 1D image in real time by reading out an electrical signal representing the X-rays detected by the plurality of AEC sensors 122 at a preset sampling rate. For example, the X-ray detector 100 may obtain the 1D image in real time by performing sampling once during a time of 100 μs or less. However, the time of 100 μs is simply an example, and the sampling time is not limited thereto.

In operation S820, the X-ray detector 100 may identify a symmetric point from the 1D image, based on a signal value for each pixel of the 1D image. The 'symmetric point' may refer, for example, to a central point about which the respective signal values of the plurality of pixels included in the 1D image are bilaterally symmetrical. According to an embodiment of the disclosure, the X-ray detector 100 may identify the symmetric point by calculating an average value of differences between a signal value of each of the plurality of pixels included in the 1D image and signal values of the other pixels spaced apart from each of the plurality of pixels and searching for a minimum value from the calculated average values. According to an embodiment of the disclosure, the X-ray detector 100 may detect a plurality of pixels corresponding to edge points from among the plurality of pixels included in the 1D image, obtain an edge point pair among the detected plurality of pixels, and identify a center point of the obtained edge point pair as the symmetric point.

In operation S830, the X-ray detector 100 may adjust respective locations of a plurality of AEC sensing areas so that the plurality of AEC sensing areas are symmetrical to each other with respect to the identified symmetric point. The AEC sensing area may be set to perform an AEC function of detecting the dose of X-rays passing through an object on an imaging surface of an X-ray detector, and blocking X-rays when the detected dose of X-rays exceeds a preset threshold. According to an embodiment of the disclosure, the plurality of AEC sensing areas may be areas pre-set by an input received from a user (e.g., a radiologist or a doctor). However, the disclosure is not limited thereto, and the plurality of AEC sensing areas may be initial default areas.

According to an embodiment of the disclosure, the X-ray detector 100 may obtain location information of a center point of the plurality of AEC sensing areas arranged on the left and right sides of the identified symmetric point, and may change the locations of the plurality of AEC sensing areas such that the location of the center point is consistent with the location of the symmetric point.

According to an embodiment of the disclosure, the X-ray detector 100 may include the plurality of AEC sensor arrays 120-1 and 120-2 of FIG. 7B. In this case, the X-ray detector 100 may obtain a symmetric axis by connecting symmetric points respectively identified by the plurality of AEC sensor arrays 120-1 and 120-2 to each other, and may adjust the locations of the plurality of AEC sensing areas so that the plurality of AEC sensing areas arranged on the left and right sides of the symmetric axis are symmetrical to each other about the symmetry axis.

Figure 9:
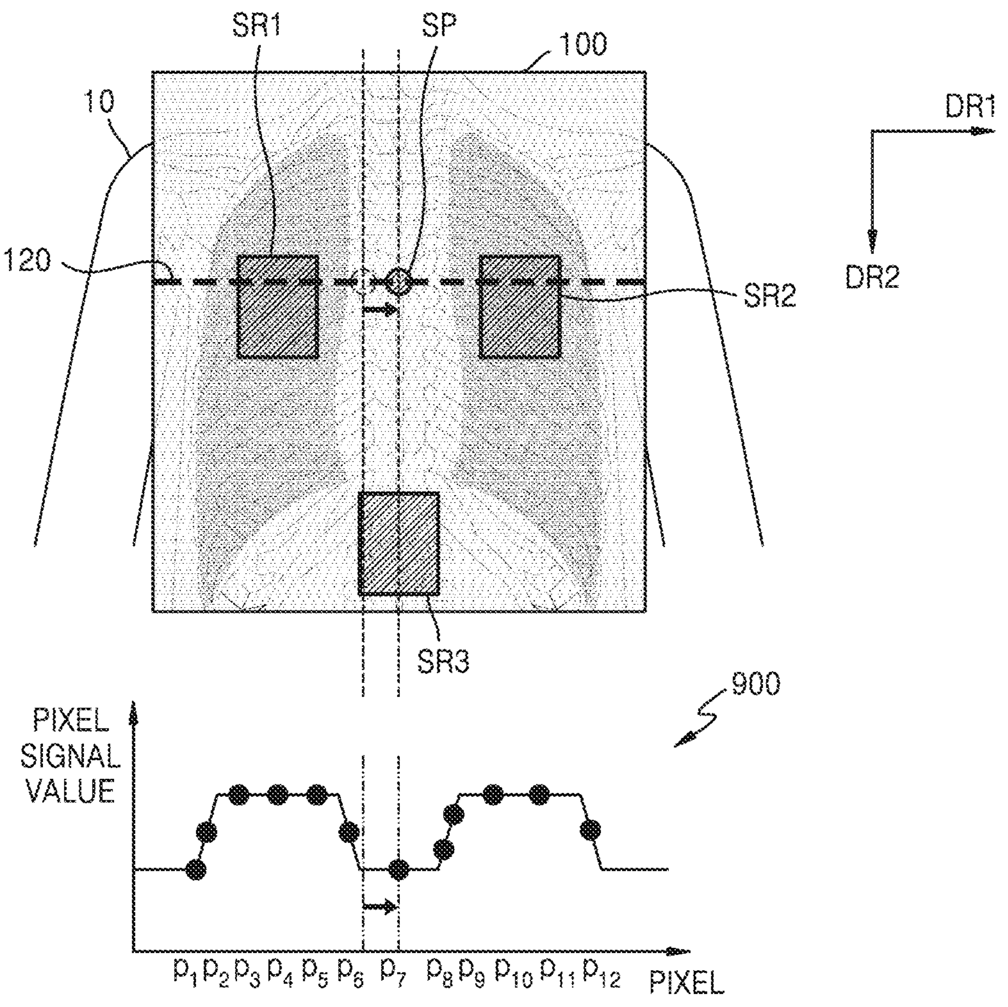
FIG. 9 is a diagram illustrating an example operation, performed by an X-ray detector, of identifying a symmetric point from a one-dimensional (1D) image, according to various embodiments.

FIG. 9 is a diagram illustrating an example operation, performed by the X-ray detector 100, of identifying a symmetric point SP from a 1D image 900, according to various embodiments.

Figure 10:
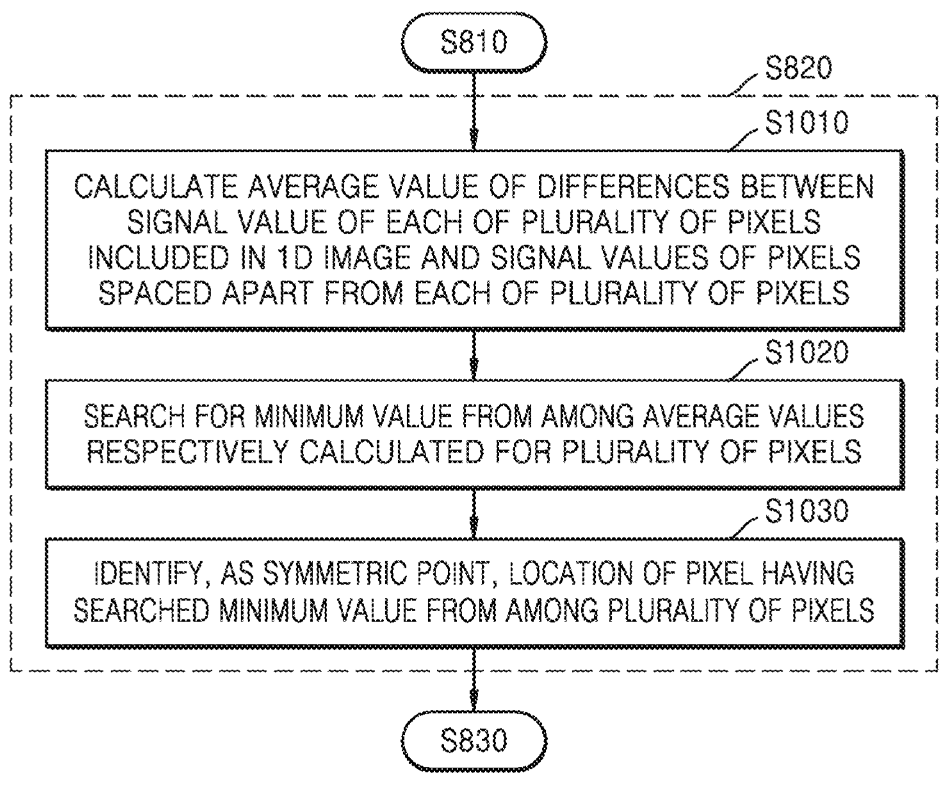
FIG. 10 is a flowchart illustrating an example operation, performed by an X-ray detector, of identifying a symmetric point from a 1D image, according to various embodiments.

FIG. 10 is a flowchart illustrating an example method, performed by the X-ray detector 100, of identifying the symmetric point SP of FIG. 9 from the 1D image 900 of FIG. 9, according to various embodiments. Operations S1010 through S1030 of FIG. 10 include details of operation S820 of FIG. 8. Operation S1010 of FIG. 10 may be performed after operation S810 of FIG. 8 is performed. Operations S830 of FIG. 8 may be performed after operation S1030 of FIG. 10 is performed.

An embodiment in which the X-ray detector 100 identifies the symmetric point SP will now be described in greater detail with reference to FIGS. 9 and 10.

Referring to FIG. 9, the X-ray detector 100 may obtain the 1D image 900 by detecting X-rays that have passed through the object through the AEC sensor array 120, converting the dose of the detected X-rays, and quantifying the electrical signal. The X-ray detector 100 may identify the symmetric point SP from the 1D image 900, based on a signal value for each pixel of the 1D image 900.

Referring to FIG. 10, in operation S1010, the X-ray detector 100 may calculate an average value of differences between a signal value of each of a plurality of pixels included in the 1D image and signal values of pixels spaced apart from each of the plurality of pixels. Referring to FIG. 10 in conjunction with FIG. 9, the processor 130 (see FIG. 5) of the X-ray detector 100 may calculate difference values between each of a plurality of pixels $p_1$ through $p_{12}$ included in the 1D image 900 and pixels spaced apart from each of the pixels $p_1$ through $p_{12}$. The processor 130 may calculate an average of the calculated difference values for each of the plurality of pixels $p_1$ through $p_{12}$. Referring to FIG. 9, the processor 130 may calculate a difference between a signal value of a second pixel $p_2$ spaced apart from a first pixel $p_1$ within the 1D image 900 and a signal value of the first pixel $p_1$, a difference between a signal value of a third pixel $p_3$ spaced apart from the first pixel $p_1$ within the 1D image 900 and the signal value of the first pixel $p_1$, a difference between a signal value of a fourth pixel $p_4$ spaced apart from the first pixel $p_1$ within the 1D image 900 and the signal value of the first pixel $p_1$, . . . , and a difference between a signal value of a twelfth pixel $p_{12}$ spaced apart from the first pixel $p_1$ within the 1D image 900 and the signal value of the first pixel $p_1$. The processor 130 may calculate an average value of the differences between the signal values of the second through twelfth pixels $p_2$ through $p_{12}$ and the signal value of the first pixel $p_1$. Similarly, the processor 130 may calculate a difference between the signal value of the first pixel $p_1$ spaced apart from the second pixel $p_2$ and the signal value of the second pixel $p_2$, a difference between the signal value of the third pixel $p_3$ spaced apart from the second pixel $p_2$ and the signal value of the second pixel $p_2$, a difference between the signal value of the fourth pixel $p_4$ spaced apart from the second pixel $p_2$ and the signal value of the second pixel $p_2$, . . . , and a difference between the signal value of the twelfth pixel $p_{12}$ spaced apart from the second pixel $p_2$ and the signal value of the second pixel $p_2$, and may calculate an average of the differences calculated based on the second pixel $p_2$. The processor 130 may perform the same operation as described above on the third through twelfth pixels $p_3$ through $p_{12}$, thereby obtaining an average value of the differences between the signal value of each of the plurality of pixels $p_1$ through $p_{12}$ and those of the other pixels spaced apart therefrom.

Referring to FIG. 9, the processor 130 calculates respective average values for the total of 12 pixels including the first through twelfth pixels $p_1$ through $p_{12}$. However, this is an example, and the disclosure is not limited thereto. According to an embodiment of the disclosure, the processor 130 may calculate the average of the differences for each of the pixels included in the 1D image 900.

In operation S1020, the X-ray detector 100 searches for a minimum value from among the average values respectively calculated for the plurality of pixels $p_1$ through $p_{12}$ of FIG. 9.

In operation S1030, the X-ray detector 100 identifies, as the symmetric point, a location of a pixel having the searched minimum value from among the plurality of pixels $p_1$ through $p_{12}$ of FIG. 9. Referring to FIG. 9, the processor 130 of the X-ray detector 100 may identify the seventh pixel $p_7$ having the minimum value among the calculated average values, and may identify a location of the seventh pixel $p_7$ as the symmetric point SP.

Figure 11:
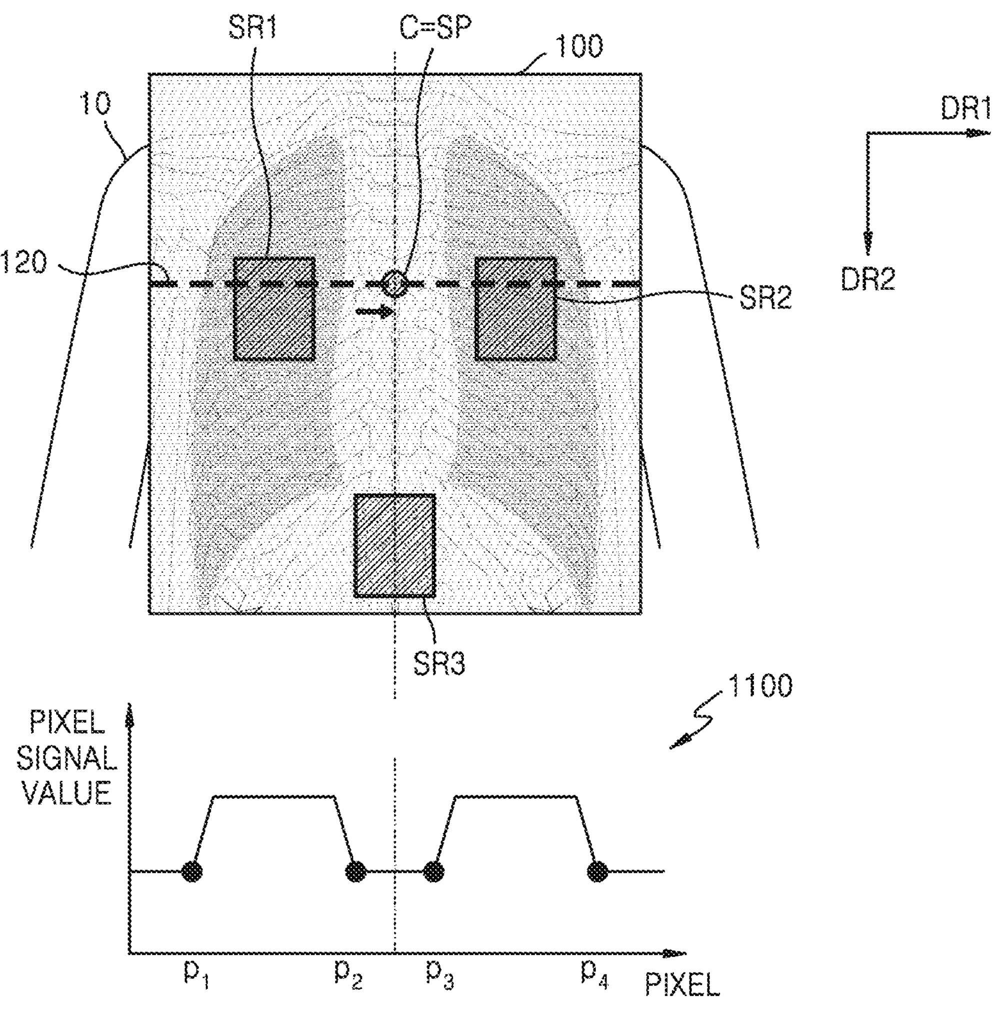
FIG. 11 is a diagram illustrating an example operation, performed by an X-ray detector, of identifying a symmetric point from a 1D image, according various embodiments.

FIG. 11 is a diagram illustrating an example operation, performed by the X-ray detector 100, of identifying a symmetric point SP from a 1D image 1100, according to various embodiments.

Figure 12:
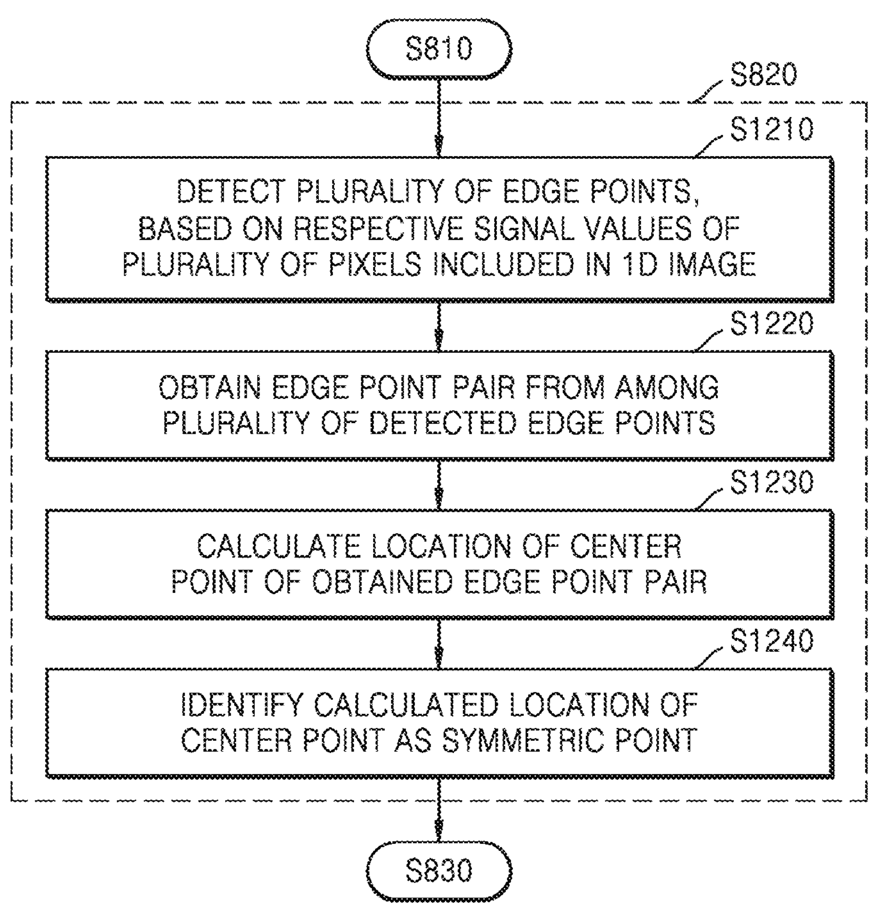
FIG. 12 is a flowchart illustrating an example operation, performed by an X-ray detector, of identifying a symmetric point from a 1D image, according to various embodiments.

FIG. 12 is a flowchart illustrating an example method, performed by the X-ray detector 100, of identifying the symmetric point SP of FIG. 11 from the 1D image 1100 of FIG. 11, according to various. Operations S1210 through S1240 of FIG. 12 include details of operation S820 of FIG. 8. Operation S1210 of FIG. 12 may be performed after operation S810 of FIG. 8 is performed. Operations S830 of FIG. 8 may be performed after operation S1240 of FIG. 12 is performed.

An embodiment in which the X-ray detector 100 identifies the symmetric point SP will now be described in greater detail with reference to FIGS. 11 and 12.

Referring to FIG. 11, the X-ray detector 100 may obtain the 1D image 1100 by detecting X-rays that have passed through the object through the AEC sensor array 120, converting the dose of the detected X-rays, and quantifying the electrical signal. The X-ray detector 100 may identify the symmetric point SP from the 1D image 1100, based on a signal value for each pixel of the 1D image 900.

Referring to FIG. 12, in operation S1210, the X-ray detector 100 may detect a plurality of edge points, based on respective signal values of a plurality of pixels included in the 1D image. The 'edge point' refers to a point where the signal values of the plurality of pixels included in the 1D image change rapidly. According to an embodiment of the disclosure, the edge point may be determined according to the anatomical part of an object 10 (see FIG. 11). For example, a difference between a signal value of a pixel related to a bone part of the object 10 and a signal value of a pixel related to a lung part of the object 10 is significantly greater than a difference between respective signal values of pixels related to the same part, so a point at a boundary between the bone part and the lung part may be identified as the edge point. In referring to FIG. 11, the processor 130 (see FIG. 5) of the X-ray detector 100 may identify, as edge points, a first pixel $p_1$, a second pixel $p_2$, a third pixel $p_3$, and a fourth pixel $p_4$ each having a significantly large difference between pixels' signal values among a plurality of pixels included in the 1D image 1100.

In operation S1220, the X-ray detector 100 may obtain an edge point pair from among the plurality of detected edge points. Referring to FIGS. 11 and 12, the processor 130 of the X-ray detector 100 may identify edge points corresponding to each other, based on the signal values of the plurality of edge points $p_1$, $p_2$, $p_3$, and $p_4$ identified from the 1D image 1100, and pair the identified edge points. For example, the processor 130 may obtain the edge point pair by pairing the first pixel $p_1$ with the fourth pixel $p_4$ among the plurality of edge points $p_1$, $p_2$, $p_3$, and $p_4$ and pairing the second pixel $p_2$ with the third pixel $p_3$.

In operation S1230, the X-ray detector 100 may calculate a location of a center point C (see FIG. 11) of the obtained edge point pair. Referring to FIGS. 11 and 12, the processor 130 of the X-ray detector 100 may identify a location of a first center point of a first edge point pair including the first pixel $p_1$ and the fourth pixel $p_4$ among the edge point pairs, and may identify a location of a second center point of a second edge point pair including the second pixel $p_2$ and the third pixel $p_3$. For example, when the locations of the first center point and the second center point are the same as each other, the processor 130 may identify the location of the first center point as the location of the center point C. As another example, when the locations of the first center point and the second center point are different from each other, the processor 130 may calculate location coordinates of the center point C using location coordinates of the first center point and location coordinates of the second center point.

In operation S1240, the X-ray detector 100 may identify the calculated location of the center point C (see FIG. 11) as the symmetric point SP (see FIG. 11). Referring to FIGS. 11 and 12, the processor 130 of the X-ray detector 100 may identify the center point C as the symmetric point SP, which is a reference point at which the plurality of AEC sensing areas SR1, SR2, and SR3 are symmetrical. According to an embodiment of the disclosure, the processor 130 may adjust the locations of the first AEC sensing area SR1 and the second AEC sensing area SR2 so that the first AEC sensing area SR1 and the second AEC sensing area SR2 among the plurality of AEC sensing areas SR1, SR2, and SR3 are bilaterally symmetrical about the symmetric point SP.

Figure 13:
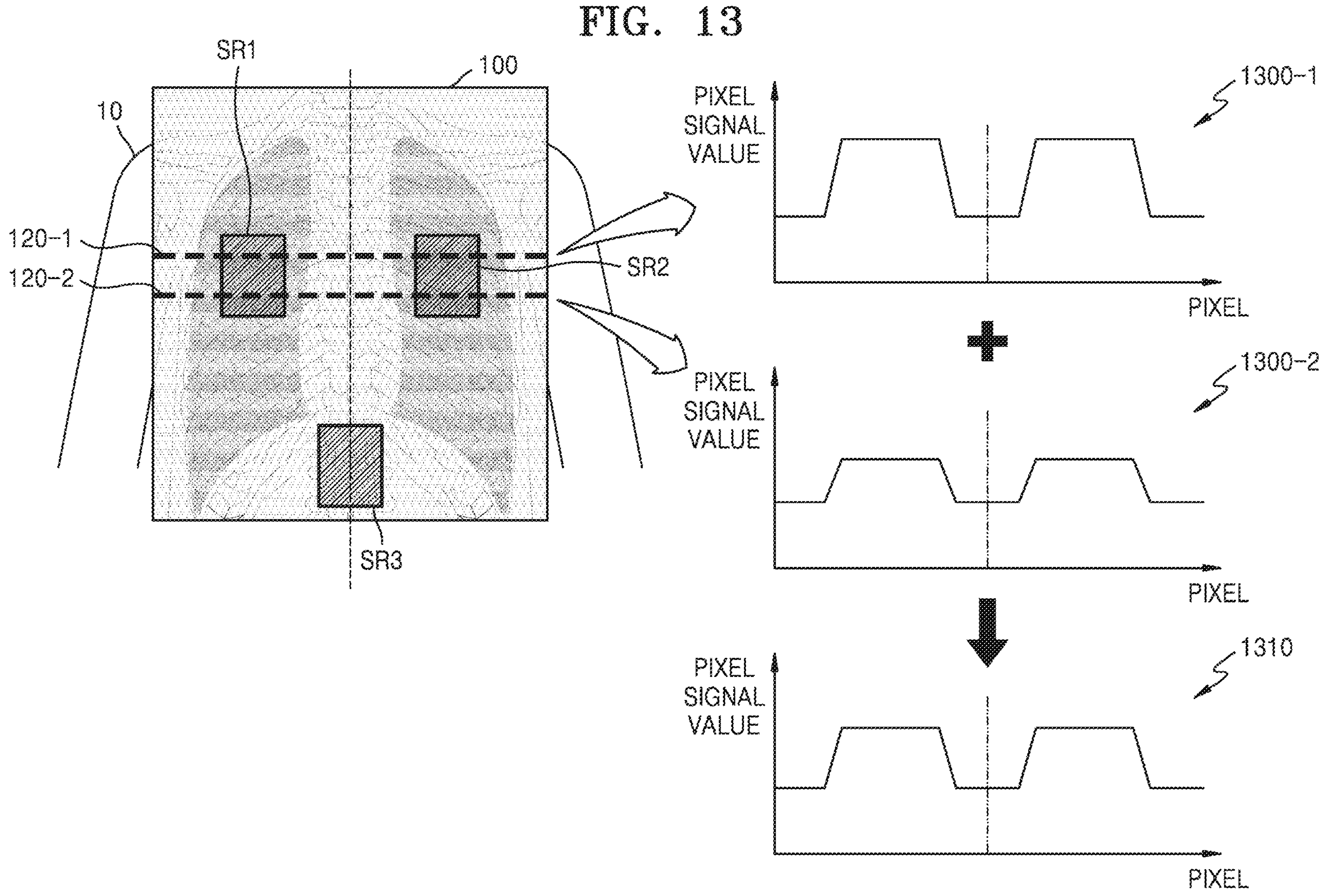
FIG. 13 is a diagram illustrating an example operation, performed by an X-ray detector, of obtaining a 1D image using a plurality of AEC sensor arrays, according to various embodiments.

FIG. 13 is a diagram illustrating an example operation, performed by the X-ray detector 100, of obtaining a 1D image 1310 using the plurality of AEC sensor arrays 120-1 and 120-2, according to various embodiments.

Referring to FIG. 13, the X-ray detector 100 may include a first AEC sensor array 120-1 and a second AEC sensor array 120-2. The first AEC sensor array 120-1 and the second AEC sensor array 120-2 may each be formed in a form of lines parallel to each other along a first direction, and may be arranged to be spaced apart from each other by a predetermined distance. FIG. 13 illustrates the X-ray detector 100 including the two AEC sensor arrays 120-1 and 120-2, but the disclosure is not limited thereto. According to an embodiment of the disclosure, the X-ray detector 100 may include one AEC sensor array or three or more AEC sensor arrays.

Each of the first AEC sensor array 120-1 and the second AEC sensor array 120-2 may include a plurality of AEC sensors 122 of FIG. 7B. Some of the plurality of AEC sensors 122 included in each of the first AEC sensor array 120-1 and the second AEC sensor array 120-2 may be disposed to be located in the plurality of AEC sensing areas SR1, SR2, and SR3.

The processor 130 (see FIG. 5) of the X-ray detector 100 may obtain a first 1D image 1300-1 by quantifying the dose of the X-rays detected using the plurality of AEC sensors 122 included in the first AEC sensor array 120-1. Similarly, the processor 130 may obtain a second 1D image 1300-2 by quantifying the dose of the X-rays detected using the plurality of AEC sensors 122 included in the second AEC sensor array 120-2. A method, performed by the X-ray detector 100, of obtaining a 1D image using a plurality of AEC sensors 122 included in an AEC sensor array is the same as that described above with reference to FIGS. 5 and 8, and thus a redundant description thereof may not be repeated here.

The X-ray detector 100 may calculate a sum of a signal values for each pixel of the first 1D image 1300-1 and a signal value for each pixel of the second 1D image 1300-2, and may obtain a 1D image 1310 resulting from the summation of the signal values for pixels. According to an embodiment of the disclosure, the processor 130 of the X-ray detector 100 may sum signal values of pixels corresponding to each other in the first 1D image 1300-1 and the second 1D image 1300-2, and obtain the 1D image 1310 representing a summed signal values for each pixel. However, the disclosure is not limited thereto. According to an embodiment of the disclosure, the processor 130 may calculate an average value of signal values for each pixel of the first 1D image 1300-1 and the second 1D image 1300-2, and may obtain the 1D image 1310 using the calculated average value for each pixel.

The X-ray detector 100 may identify a symmetric point, based on the respective signal values of the plurality of pixels included in the 1D image 1310. A method, performed by the processor 100, of identifying the symmetric point from the 1D image 1310 is the same as or similar to that described above with reference to FIGS. 5 and 8 through 12, and thus a redundant description thereof may not be repeated here.

Figure 14:
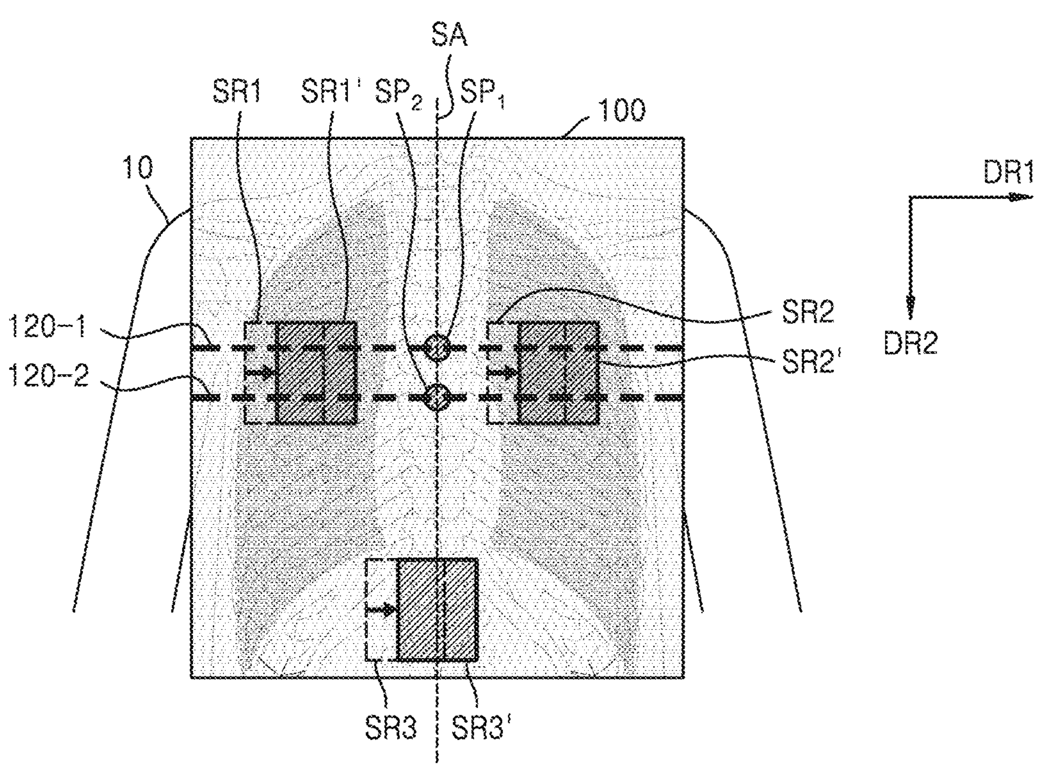
FIG. 14 is a diagram illustrating an example operation, performed by an X-ray detector, of adjusting respective locations of a plurality of AEC sensing areas, based on a symmetric point, according to various embodiments.

FIG. 14 is a diagram illustrating an example operation, performed by the X-ray detector 100, of adjusting respective locations of a plurality of AEC sensing areas SR1, SR2, and SR3, based on a symmetric point, according to various embodiments.

Referring to FIG. 14, the X-ray detector 100 may include a first AEC sensor array 120-1 and a second AEC sensor array 120-2. The first AEC sensor array 120-1 and the second AEC sensor array 120-2 may each be formed in a form of lines parallel to each other along the first direction DR1, and may be arranged to be spaced apart from each other by a predetermined distance. Descriptions of the first AEC sensor array 120-1 and the second AEC sensor array 120-2 are the same as those given with reference to FIGS. 7B and 13, and thus a redundant description thereof may not be repeated here.

The processor 130 (see FIG. 5) of the X-ray detector 100 may obtain a 1D image by quantifying the dose of the X-rays detected using the plurality of AEC sensors 122 of FIG. 7B included in the first AEC sensor array 1201, and may identify a first symmetric point $SP_1$ based on a signal value for each pixel of the 1D image. Similarly, the processor 130 may obtain a 1D image by quantifying the dose of the X-rays detected using the plurality of AEC sensors 122 included in the second AEC sensor array 120-2, and may identify a second symmetric point $SP_2$ based on a signal value for each pixel of the 1D image. Referring to FIG. 14, the processor 130 identifies the two symmetric points $SP_1$ and $SP_2$. However, the disclosure is not limited thereto. According to an embodiment of the disclosure, the X-ray detector 100 includes three or more AEC sensor arrays, and the processor 130 may identify three or more symmetric points from a plurality of 1D images respectively obtained from the three or more AEC sensor arrays. A method, performed by the processor 130, of identifying a symmetric point based on a signal value for each pixel of a 1D image is the same as or similar to that described above with reference to FIGS. 5 and 8 through 12, and thus a redundant description thereof may not be repeated here.

The X-ray detector 100 may obtain a symmetric axis SA by connecting the identified first symmetric point $SP_1$ and the identified second symmetric point $SP_2$. The symmetric axis SA is a virtual straight line connecting a plurality of symmetric points $SP_1$ and $SP_2$, and may extend along, for example, the second direction DR2.

The X-ray detector 100 may adjust the respective locations of the plurality of AEC sensing areas SR1, SR2, and SR3, such that the plurality of AEC sensing areas SR1, SR2, and SR3 are symmetrical about the symmetric axis SA. Referring to FIG. 14, the X-ray detector 100 may include three AEC sensing areas SR1, SR2, and SR3. However, the disclosure is not limited thereto. The processor 130 (see FIG. 5) of the X-ray detector 100 may change the location of the first AEC sensing area SR1 to SR1' and change the location of the second AEC sensing area SR2 to SR2' such that the first AEC sensing area SR1 and the second AEC sensing area SR2 disposed on the left and right sides of the symmetric axis SA are bilaterally symmetrical to each other about the symmetric axis SA. The processor 130 may change the location of the third AEC sensing area SR3 to SR3' such that the area size of the third AEC sensing area SR3 is the same on the left and right sides of the symmetric axis SA.

Figure 15:
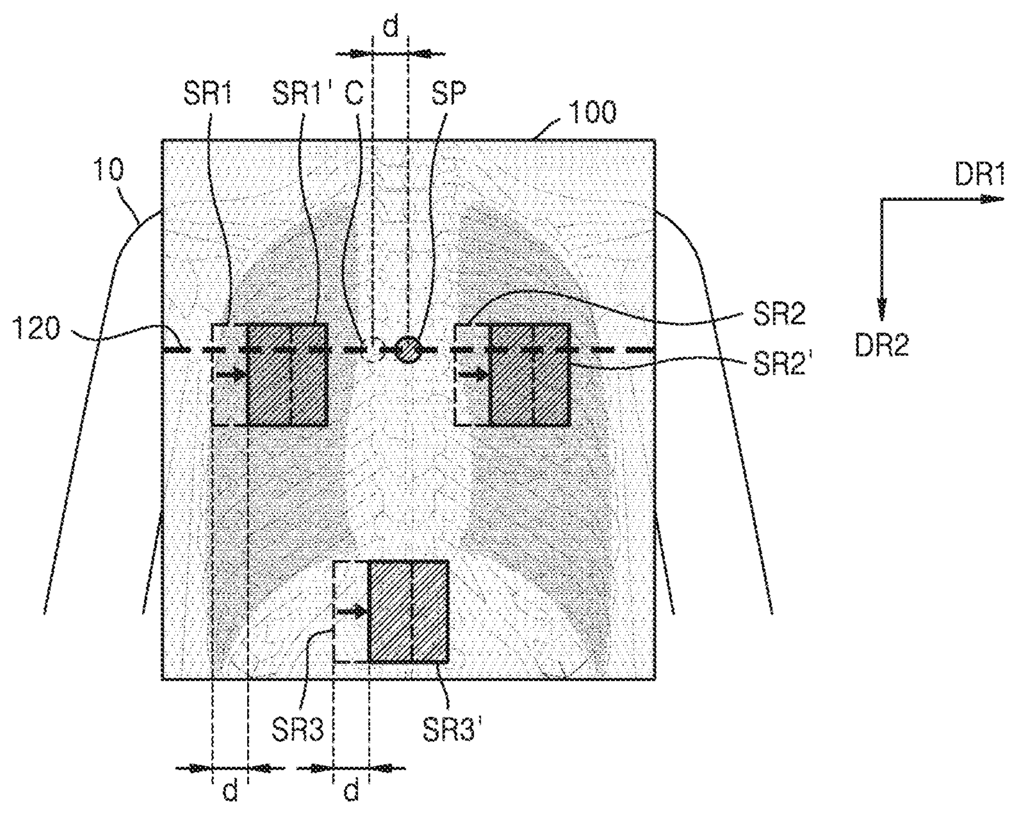
FIG. 15 is a diagram illustrating an example operation, performed by an X-ray detector, of adjusting respective locations of a plurality of AEC sensing areas, based on a symmetric point, according to various embodiments.

FIG. 15 is a diagram illustrating an example operation, performed by the X-ray detector 100, of adjusting respective locations of a plurality of AEC sensing areas SR1, SR2, and SR3, based on a symmetric point SP, according to various embodiments.

Referring to FIG. 15, the X-ray detector 100 may include an AEC sensor array 120, and may obtain a 1D image using the AEC sensor array 120. The X-ray detector 100 may identify the symmetric point SP, based on the respective signal values of the plurality of pixels included in the 1D image.

The X-ray detector 100 may obtain information about a location of a center point C of the first and second AEC sensing areas SR1 and SR2 arranged on the left and right sides of the symmetric point SP among the plurality of AEC sensing areas SR1, SR2, and SR3. According to an embodiment of the disclosure, the processor 130 (see FIG. 5) of the X-ray detector 100 may calculate a location coordinate value of the center point C using location coordinate values of a plurality of pixels included in the first AEC sensing area SR1 and location coordinate values of their corresponding pixels among location coordinate values of a plurality of pixels included in the second AEC sensing area SR2.

The X-ray detector 100 may change the respective locations of the plurality of AEC sensing areas SR1, SR2, and SR3, such that the obtained location of the center point C coincides with the location of the symmetric point SP. The processor 130 of the X-ray detector 100 may obtain information on a distance d, which is a displacement value between the location of the central point C and the location of the symmetric point SP, and may obtain information on relative directions of the central point C and the symmetric point SP. According to an embodiment of the disclosure, the processor 130 of the X-ray detector 100 may calculate a difference between the location coordinate value of the center point C and the location coordinate value of the symmetric point SP, and calculate a value of the distance d, based on the difference. The processor 130 may also obtain relative direction information between the center point C and the symmetric point SP. Referring FIG. 15, the center point C is located on the left side of the symmetric point SP. However, the disclosure is not limited thereto, and the center point C may be located on any of the right, upper, or lower side of the symmetric point SP. The processor 130 may move the respective locations of the first AEC sensing area SR1 and the second AEC sensing area SR2 disposed on the left and right sides of the symmetric point SP by the distance d to change the respective locations of the first AEC sensing area SR1 and the second AEC sensing area SR2 to SR1' and SR2, respectively. The processor 130 may change the respective locations of the first AEC sensing area SR1 and the second AEC sensing area SR2 to SR1' and SR2, respectively, based on the relative direction information between the center point C and the symmetric point SP. Referring to FIG. 15, the X-ray detector 130 may move the respective locations of the first AEC sensing area SR1 and the second AEC sensing area SR2 rightwards.

The X-ray detector 100 may change a location of the third AEC sensing area SR3 by the same displacement value as a displacement value of each of the first AEC sensing area SR1 and the second AEC sensing area SR2. Referring to FIG. 15, the X-ray detector 130 of the X-ray detector 100 may change the location of the third AEC sensing area SR3 to SR3' by moving the location of the third AEC sensing area SR3 by the distance d rightwards.

FIG. 15 illustrates an embodiment of adjusting the respective locations of the plurality of AEC sensing areas SR1, SR2, and SR3, based on a positional relationship between the one symmetric point SP and the center point C, but the disclosure is not limited thereto. According to an embodiment of the disclosure, the X-ray detector 100 may adjust the respective locations of the plurality of AEC sensing areas SR1, SR2, and SR3, based on positional relationships between a plurality of symmetric points SP or the symmetric axis SA (see FIG. 14) and the center point C.

In the examples illustrated in FIGS. 14 and 15, the X-ray detector 100 adjusts the respective locations of the plurality of AEC sensing areas SR1, SR2, and SR3, based on the symmetric point SP or the symmetric axis SA, thereby addressing distortion of the alignment between the patient's anatomical location and the X-ray detector 100 and improving alignment accuracy. Accordingly, the X-ray detector 100 according to the disclosure may prevent and/or reduce X-ray over-radiation on a patient and provide a technical effect of obtaining a high-quality X-ray image. In addition, the X-ray detector 100 according to an embodiment of the disclosure may prevent and/or reduce retake due to failure to predict the amount of X-ray radiation, and reduce the average dose of X-rays radiated during photographing.

Figure 16:
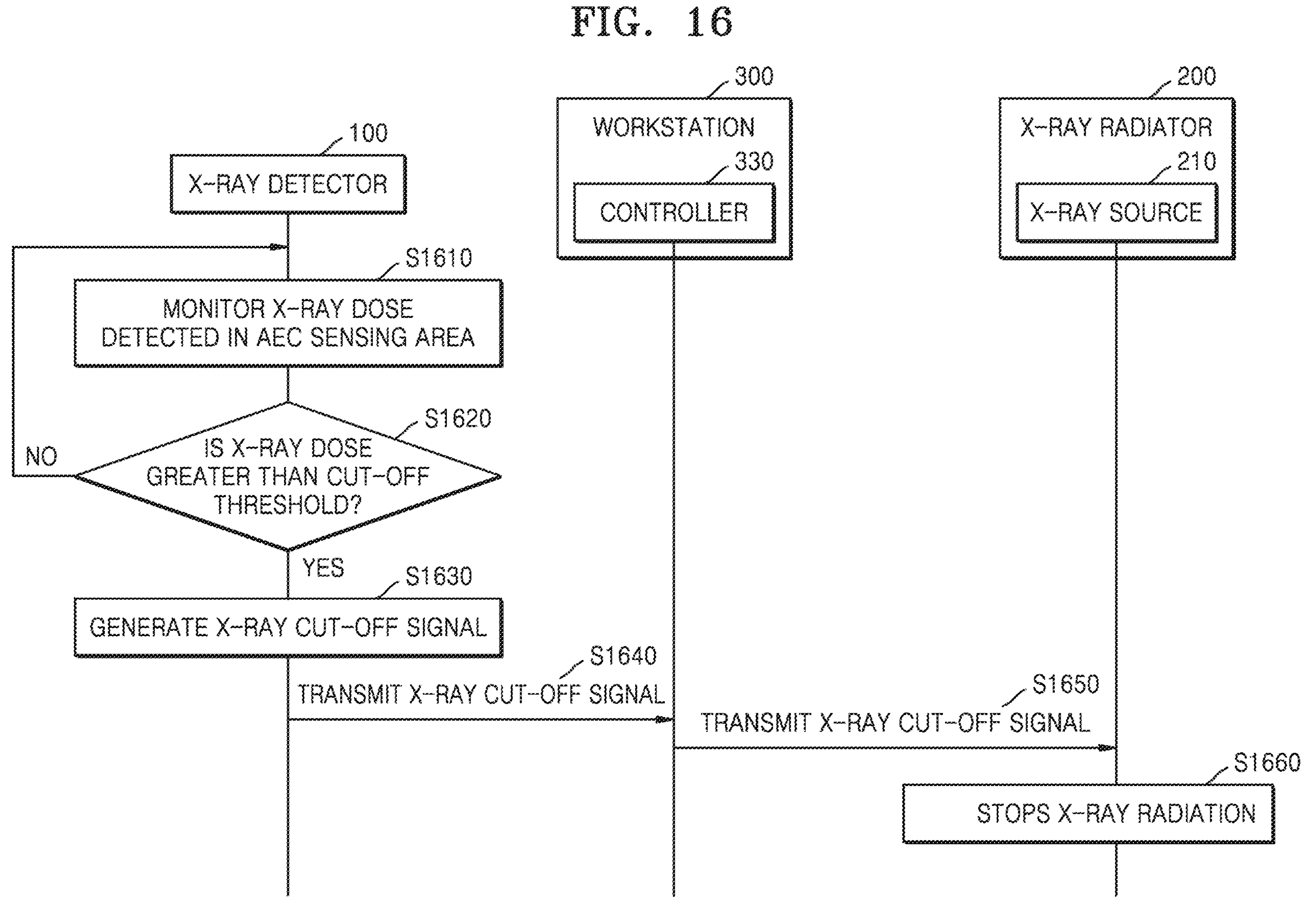
FIG. 16 is a signal flow diagram including a flowchart illustrating an example method of operating an X-ray detector, an X-ray radiator, and a workstation, according to various embodiments.

FIG. 16 is a signal flow diagram including a flowchart illustrating an example method of operating the X-ray detector 100, the X-ray radiator 200, and the workstation 300, according to various embodiments.

FIG. 16 illustrates a flow of operations performed by the X-ray detector 100 after adjusting the respective locations of the plurality of AEC sensing areas SR1, SR2, and SR3 (see FIGS. 14 and 15), according to an embodiment of the disclosure. Operation S1610 of FIG. 16 may be performed after operation S830 of FIG. 8 is performed.

In operation S1610, the X-ray detector 100 monitors an X-ray dose detected in an AEC sensing area. The X-ray detector 100 may monitor the numerical value of an electrical signal indicating the dose of the X-ray detected by an AEC sensor in the location-adjusted AEC sensing areas SR1', SR2', and SR3' (see FIGS. 14 and 15).

In operation S1620, the X-ray detector 100 compares the monitored X-ray dose with a preset cut-off threshold.

In operation S1630, when the X-ray dose exceeds the cut-off threshold, the X-ray detector 100 generates an X-ray cut-off signal. The 'X-ray cut-off signal' is an electrical signal that commands blockage of emission and radiation of X-rays.

In operation S1640, the X-ray detector 100 transmits the X-ray cut-off signal to the controller 330 of the workstation 300. The X-ray detector 100 may be connected to the workstation 300 through a wired communication network or a wireless communication network, and may transmit the X-ray cut-off signal to the workstation. According to an embodiment of the disclosure, when the X-ray detector 100 is implemented as a mobile detector, the X-ray detector 100 may transmit the X-ray cut-off signal to the workstation 300 using at least one wireless data communication network from among, for example, a wired LAN, a wireless LAN, Wi-Fi, Bluetooth, Zigbee, Wi-Fi Direct (WFD), Bluetooth Low Energy (BLE), Wireless Broadband Internet (Wibro), World Interoperability for Microwave Access (WiMAX), a shared wireless access protocol (SWAP), Wireless Gigabit Alliance (WiGig), and RF communication.

In operation S1650, the controller 330 of the workstation 300 transmits the X-ray cut-off signal to the X-ray radiator 200.

In operation S1660, the X-ray radiator 200 stops the X-ray radiation. According to an embodiment of the disclosure, the X-ray radiator 200 may stop the X-ray radiation by controlling a high voltage generator (HVG) to stop generating a high voltage and blocking X-rays that are transmitted from the HVG to the X-ray source 210.

The disclosure provides an X-ray detector that includes an AEC sensor and corrects an AEC sensing area. The X-ray detector 100 may include a plurality of photodetection elements 110 including a plurality of pixels and configured to detect X-rays, an AEC sensor array 120 configured to detect X-rays that have passed through an object and to quantify a dose of the detected X-rays as a signal value and output the signal value, a memory 140 storing one or more instructions, and at least one processor, comprising processing circuitry 130, individually and/or collectively, configured to execute the at least one instruction stored in the memory 140. At least one processor 130, individually and/or collectively, may be configured to obtain a 1D image, based on the signal value output through the AEC sensor array 120. At least one processor 130, individually and/or collectively, may be configured to identify a symmetric point from the 1D image, based on a signal value for each pixel of the 1D image. At least one processor 130, individually and/or collectively, may be configured to adjust respective locations of a plurality of AEC sensing areas 120 so that the plurality of AEC sensing areas 120 are symmetrical to each other with respect to the identified symmetric point. According to an example embodiment of the disclosure, the AEC sensor array 120 may be a line-type sensor array including the plurality of photodetection elements 120 arranged in a first direction among the plurality of photodetection elements 110 included in the X-ray detector 100.

According to an embodiment of the disclosure, the AEC sensor array 120 may include a plurality of AEC sensors, and at least one AEC sensor among the plurality of AEC sensors may be located within the plurality of AEC sensing areas.

According to an embodiment of the disclosure, at least one processor 130, individually and/or collectively, may be configured to calculate an average value of differences between a signal value of each of a plurality of pixels included in the 1D image and respective signal values of pixels spaced apart from each of the plurality of pixels included in the 1D image. At least one processor 130, individually and/or collectively, may be configured to search for a minimum value among the average values respectively calculated for the plurality of pixels, At least one processor 130, individually and/or collectively, may be configured to identify a location of a pixel having the searched minimum value among the plurality of cells as the symmetric point.

According to an embodiment of the disclosure, at least one processor 130, individually and/or collectively, may be configured to detect a plurality of edge points based on the signal values of the plurality of pixels of the 1D image. At least one processor 130, individually and/or collectively, may be configured to obtain an edge point pair among the detected plurality of edge points, At least one processor 130, individually and/or collectively, may be configured to calculate a location of a center point of the obtained edge point pair. At least one processor 130, individually and/or collectively, may be configured to identify the location of the calculated center point as the symmetric point.

According to an embodiment of the disclosure, the AEC sensor array 120 may include a first AEC sensor array and a second AEC sensor array arranged in the form of parallel lines. At least one processor 130, individually and/or collectively, may be configured to identify the symmetric point using a sum of a signal value for each pixel of a first 1D image obtained using the first AEC sensor array and a signal value for each pixel of a second 1D image obtained using the second AEC sensor array.

According to an embodiment of the disclosure, the AEC sensor array 120 may include a plurality of arrays. At least one processor 130, individually and/or collectively, may be configured to identify a plurality of symmetric points from the 1D image obtained using a plurality of AEC sensor arrays, At least one processor 130, individually and/or collectively, may be configured to obtain a symmetric axis by connecting the plurality of symmetric points to each other, and change respective locations of the plurality of AEC sensing areas so that the plurality of AEC sensing areas arranged on left and right sides of the symmetric axis are symmetrical to each other about the symmetric axis.

According to an embodiment of the disclosure, at least one processor 130, individually and/or collectively, may be configured to obtain a location of a center point of the plurality of AEC sensing areas arranged on the left and right sides of the identified symmetric point. At least one processor 130, individually and/or collectively, may be configured to change respective locations of the plurality of AEC sensing areas such that the location of the center point is consistent with the location of the symmetric point.

According to an embodiment of the disclosure, at least one processor 130, individually and/or collectively, may be configured to obtain a 1D image in real time by reading out X-rays detected through a plurality of AEC sensors included in the AEC sensor array 120 at a preset sampling rate. At least one processor 130, individually and/or collectively, may be configured to identify the symmetric point in real time according to the obtained 1D image and adjust the locations of the plurality of AEC sensing areas.

According to an embodiment of the disclosure, the X-ray detector 100 may further include the communication interface 150, and at least one processor 130, individually and/or collectively, may be configured to control the communication interface 150 to compare the dose of X-rays detected by the plurality of location-adjusted AEC sensing areas with a preset cut-off threshold and, when the dose of the detected X-rays exceeds the cut-off threshold, transmit a X-ray cut-off signal to an X-ray source controller.

The disclosure provides a method of operating the X-ray detector 100 including an AEC sensor. The method of operating the X-ray detector 100 may include detecting X-rays that have passed through an object, using the AEC sensor array 120, and obtaining a 1D image by quantifying a dose of the detected X-rays into a signal value. The method of operating the X-ray detector 100 may include identifying a symmetric point from the 1D image, based on a signal value for each pixel of the 1D image. The method of operating the X-ray detector 100 may include adjusting respective locations of a plurality of AEC sensing areas so that the plurality of AEC sensing areas are symmetrical to each other with respect to the identified symmetric point.

According to an embodiment of the disclosure, the identifying of the symmetric point may include calculating an average value of differences between a signal value of each of a plurality of pixels included in the 1D image and respective signal values of pixels spaced apart from the each of the plurality of pixels included in the 1D image; searching for a minimum value among average values respectively calculated for the plurality of pixels; and identifying a location of a pixel having the searched minimum value among the plurality of pixels as the symmetric point.

According to an embodiment of the disclosure, the identifying of the symmetric point may include: detecting a plurality of edge points, based on the signal values of the plurality of pixels of the 1D image; obtaining an edge point pair from among the plurality of detected edge points; calculating a location of a center point of the obtained edge point pair; and identifying the location of the center point as the symmetric point.

According to an embodiment of the disclosure, the AEC sensor array 120 may include a first AEC sensor array and a second AEC sensor array arranged in the form of parallel lines. The identifying the symmetric point may include: identifying the symmetric point using a sum of a signal value for each pixel of a first 1D image obtained using the first AEC sensor array and a signal value for each pixel of a second 1D image obtained using the second AEC sensor array.

According to an embodiment of the disclosure, the identifying the symmetric point may include identifying a plurality of symmetric points from the 1D image obtained using a plurality of AEC sensor arrays 120; and obtaining a symmetric axis by connecting the plurality of symmetry points to each other. The adjusting the locations of the plurality of AEC sensing areas may include changing the locations of the plurality of AEC sensing areas such that the plurality of AEC sensing area arranged on left and right sides of the symmetric axis are symmetrical to each other about the symmetric axis.

According to an embodiment of the disclosure, the adjusting the locations of the plurality of AEC sensing areas may include obtaining a location of a center point of the plurality of AEC sensing areas arranged on the left and right sides of the identified symmetric point; and changing the locations of the plurality of AEC sensing areas so that the location of the obtained center point is consistent with the location of the symmetric point.

According to an embodiment of the disclosure, the X-ray detector 100 may further include the communication interface 150, and at least one processor 130 may control the communication interface 150 to compare the dose of X-rays detected by the plurality of location-adjusted AEC sensing areas with a preset cut-off threshold and, when the dose of the detected X-rays exceeds the cut-off threshold, transmit a X-ray cut-off signal to an X-ray source controller.

An example embodiment of the disclosure provides a computer program product including a non-transitory computer-readable recording medium having recorded thereon a computer program. The storage medium may include instructions regarding the operations of: detecting X-rays that have passed through an object, using an AEC sensor array 120, and obtaining a 1D image by quantifying a dose of the detected X-rays into a signal value; identifying a symmetric point from the 1D image, based on a signal value for each pixel of the 1D image; and adjusting respective locations of a plurality of AEC sensing areas so that the plurality of AEC sensing areas are symmetrical to each other with respect to the identified symmetric point.

The program executed by the X-ray detector 100 or X-ray imaging apparatus 1000 described above herein may be implemented as a hardware component, a software component, and/or a combination of hardware components and software components. The program may be executed by any system capable of executing computer readable instructions.

The software may include a computer program, a code, instructions, or a combination of one or more of the foregoing, and may comprise a processing device so that the processing device can operate as desired, or may independently or collectively instruction the processing device.

The software may be implemented as a computer program including instructions stored in computer-readable storage media. Examples of the computer-readable recording media include magnetic storage media (e.g., ROM, floppy disks, hard disks, etc.), and optical recording media (e.g., CD-ROMs, or digital versatile discs (DVDs)). The computer-readable storage media can be distributed over network coupled computer systems so that the computer-readable code is stored and executed in a distributive manner. These media can be read by the computer, stored in a memory, and executed by a processor.

The computer-readable storage medium may be provided as a non-transitory storage medium. Wherein the, 'non-transitory' storage medium may not include a signal and is tangible, but does not distinguish whether data is stored semi-permanently or temporarily in the storage medium. For example, the non-transitory recording medium may include a buffer in which data is temporarily stored.

Programs according to various embodiments disclosed herein may be provided by being included in computer program products. The computer program product, which is a commodity, may be traded between sellers and buyers.

Computer program products may include a software program and a computer-readable storage medium having the software program stored thereon. For example, computer program products may include a product in the form of a software program (e.g., a downloadable application) that is electronically distributed through electronic device manufacturers or electronic markets (e.g., Samsung Galaxy Store). For electronic distribution, at least a portion of the software program may be stored on a storage medium or may be created temporarily. In this case, the storage medium may be a server or a storage medium of a relay server for temporarily storing a software program.

The computer program product may include a storage medium of the X-ray detector 100 and/or of the X-ray imaging device 1000 including the X-ray detector 100. Alternatively, if there is a third device (e.g., a mobile device) in communication with the X-ray detector 100, the computer program product may include a storage medium of the third device. The computer program product may include the software program itself transmitted from the X-ray detector 100 to the third device, or transmitted from the third device to the X-ray detector 100.

In this case, at least one of the X-ray detector 100 or the X-ray imaging device 1000 may execute the computer program product to perform the methods according to the disclosed embodiments. Alternatively, at least two of the X-ray detector 100, the X-ray imaging device 1000, or the third device may execute the computer program product to distribute and perform the methods according to the disclosed embodiments.

For example, the X-ray detector 100 may control another electronic device (e.g., a mobile device) in communication with the X-ray detector 100 to perform the methods according to the disclosed embodiments, by executing the computer program product stored in the memory 140 of FIG. 5.

As another example, a third device may execute a computer program product to control an electronic device in communication with the third device to perform the methods according to the disclosed embodiments.

When the third device executes the computer program product, the third device may download the computer program product from the X-ray detector 100 and execute the downloaded computer program product. The third device may execute a computer program product provided in a preloaded state to perform methods according to the disclosed embodiments.

While the disclosure has been illustrated and described with reference to various example embodiments thereof, it will be understood by those of ordinary skill in the art that various changes in form and details may be made therein without departing from the spirit and scope of the disclosure including the appended claims and their equivalents. For example, an appropriate result may be attained even when the above-described techniques are performed in a different order from the above-described method, and/or components, such as the above-described computer system or module, are coupled or combined in a different form from the above-described methods or substituted for or replaced by other components or equivalents thereof. It will also be understood that any of the embodiment(s) described herein may be used in conjunction with any other embodiment(s) described herein.

What is claimed is:

1. An X-ray detector comprising:

a plurality of photodetection elements including a plurality of pixels and configured to detect X-rays;

an automatic exposure control (AEC) sensor array including at least one AEC sensor configured to detect X-rays that have passed through an object and to quantify a dose of the detected X-rays as a signal value and output the signal value;

a memory storing one or more instructions; and at least one processor, comprising processing circuitry, configured to execute the one or more instructions stored in the memory, wherein at least one processor, individually and/or collectively, is configured to:

obtain a one-dimensional (1D) image, based on the signal value output by the AEC sensor array, identify a symmetric point from the 1D image, based on a signal value for each pixel of the 1D image, and adjust respective locations of a plurality of AEC sensing areas so that the plurality of AEC sensing areas are symmetrical to each other with respect to the identified symmetric point.

2. The X-ray detector of claim 1, wherein the AEC sensor array comprises a line-type sensor array including a plurality of photodetection elements arranged in a first direction among the plurality of photodetection elements included in the X-ray detector.

3. The X-ray detector of claim 1, wherein the AEC sensor array includes a plurality of AEC sensors, and at least one AEC sensor among the plurality of AEC sensors is located within the plurality of AEC sensing areas.

4. The X-ray detector of claim 1, wherein at least one processor, individually and/or collectively, is configured to: calculate an average value of differences between a signal value of each of a plurality of pixels included in the 1D image and respective signal values of pixels spaced apart from each of the plurality of pixels included in the 1D image, search for a minimum value among the average values respectively calculated for the plurality of pixels, and identify, among the plurality of cells, a location of a pixel having the minimum value as the symmetric point.

5. The X-ray detector of claim 1, wherein at least one processor, individually and/or collectively, is configured to: detect a plurality of edge points based on the signal values of the plurality of pixels of the 1D image, obtain an edge point pair among the detected plurality of edge points, calculate a location of a center point of the obtained edge point pair, and identify the location of the calculated center point as the symmetric point.

6. The X-ray detector of claim 1, wherein the AEC sensor array includes a first AEC sensor array and a second AEC sensor array arranged in parallel lines, and at least one processor, individually and/or collectively, is configured to identify the symmetric point using a sum of a signal value for each pixel of a first 1D image obtained using the first AEC sensor array and a signal value for each pixel of a second 1D image obtained using the second AEC sensor array.

7. The X-ray detector of claim 1, wherein the AEC sensor array includes a plurality of arrays, and at least one processor, individually and/or collectively, is configured to:

identify a plurality of symmetric points from the 1D image obtained using a plurality of AEC sensor arrays, obtain a symmetric axis by connecting the plurality of symmetric points to each other, and change respective locations of the plurality of AEC sensing areas so that the plurality of AEC sensing areas arranged on left and right sides of the symmetric axis are symmetrical to each other about the symmetric axis.

8. The X-ray detector of claim 1, wherein at least one processor, individually and/or collectively, is configured to: obtain a location of a center point of the plurality of AEC sensing areas arranged on the left and right sides of the identified symmetric point, and change respective locations of the plurality of AEC sensing areas such that the location of the center point is consistent with the location of the symmetric point.

9. A method of operating an X-ray detector including an automatic exposure control (AEC) sensor, the method comprising:

detecting, using an AEC sensor array, X-rays that have passed through an object, and obtaining a one-dimensional (1D) image by quantifying a dose of the detected X-rays into a signal value;

identifying a symmetric point from the 1D image, based on a signal value for each pixel of the 1D image; and adjusting respective locations of a plurality of AEC sensing areas so that the plurality of AEC sensing areas are symmetrical to each other with respect to the identified symmetric point.

10. The method of claim 9, wherein the identifying of the symmetric point comprises:

calculating an average value of differences between a signal value of each of a plurality of pixels included in the 1D image and respective signal values of pixels spaced apart from each of the plurality of pixels included in the 1D image;

searching for a minimum value among average values respectively calculated for the plurality of pixels; and identifying a location of a pixel having the minimum value among the plurality of pixels as the symmetric point.

11. The method of claim 9, wherein the identifying of the symmetric point comprises:

detecting a plurality of edge points, based on the signal values of the plurality of pixels of the 1D image;

obtaining an edge point pair from among the plurality of detected edge points;

calculating a location of a center point of the obtained edge point pair; and identifying the location of the center point as the symmetric point.

12. The method of claim 9, wherein the AEC sensor array includes a first AEC sensor array and a second AEC sensor array arranged in parallel lines, and the identifying of the symmetric point comprises identifying the symmetric point using a sum of a signal value for each pixel of a first 1D image obtained using the first AEC sensor array and a signal value for each pixel of a second 1D image obtained using the second AEC sensor array.

13. The method of claim 9, wherein the identifying of the symmetric point comprises:

identifying a plurality of symmetric points from the 1D image obtained using a plurality of AEC sensor arrays; and obtaining a symmetric axis by connecting the plurality of symmetry points to each other, and the adjusting of the locations of the plurality of AEC sensing areas comprises changing the locations of the plurality of AEC sensing areas such that the plurality of AEC sensing areas arranged on left and right sides of the symmetric axis are symmetrical to each other about the symmetric axis.

14. The method of claim 9, wherein the adjusting of the respective locations of a plurality of AEC sensing areas comprises:

obtaining a location of a center point of the plurality of AEC sensing areas arranged on the left and right sides of the identified symmetric point; and changing the locations of the plurality of AEC sensing areas so that the location of the obtained center point is consistent with the location of the symmetric point.

15. A computer program product including a non-transitory computer-readable storage medium storing instructions readable by an X-ray detector including an automatic exposure control (AEC) sensor, the instructions, when executed by at least one processor, individually and/or collectively, of the X-ray detector, cause the X-ray detector to perform operations including:

detecting, using an AEC sensor array, X-rays that have passed through an object, and obtaining a one-dimensional (1D) image by quantifying a dose of the detected X-rays into a signal value;

identifying a symmetric point from the 1D image, based on a signal value for each pixel of the 1D image; and adjusting respective locations of a plurality of AEC sensing areas so that the plurality of AEC sensing areas are symmetrical to each other with respect to the identified symmetric point.

* * * * *